US008732188B2

(12) United States Patent
Doniger et al.

(10) Patent No.: US 8,732,188 B2
(45) Date of Patent: May 20, 2014

(54) METHOD AND SYSTEM FOR PROVIDING CONTEXTUAL BASED MEDICATION DOSAGE DETERMINATION

(75) Inventors: Kenneth J. Doniger, Menlo Park, CA (US); Mark K. Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 189 days.

(21) Appl. No.: 12/032,617

(22) Filed: Feb. 15, 2008

(65) Prior Publication Data

US 2008/0201325 A1 Aug. 21, 2008

Related U.S. Application Data

(60) Provisional application No. 60/890,492, filed on Feb. 18, 2007.

(51) Int. Cl.
*G06F 7/00* (2006.01)
*G06F 17/30* (2006.01)
*G06Q 50/00* (2012.01)

(52) U.S. Cl.
USPC ................................................ 707/769; 705/3

(58) Field of Classification Search
USPC ........... 707/780, E17.044, E17.014, E17.017, 707/E17.016, 999.003; 705/3; 715/771, 968
See application file for complete search history.

(56) References Cited

U.S. PATENT DOCUMENTS

| | | | |
|---|---|---|---|
| 2,755,036 | A | 7/1956 | Mikko |
| 3,260,656 | A | 7/1966 | Ross, Jr. |
| 3,304,413 | A | 2/1967 | Lehmann et al. |
| 3,581,062 | A | 5/1971 | Aston |
| 3,651,318 | A | 3/1972 | Czekajewski |
| 3,653,841 | A | 4/1972 | Klein |
| 3,698,386 | A | 10/1972 | Fried |
| 3,719,564 | A | 3/1973 | Lilly, Jr. et al. |
| 3,768,014 | A | 10/1973 | Smith et al. |
| 3,776,832 | A | 12/1973 | Oswin et al. |
| 3,837,339 | A | 9/1974 | Aisenberg et al. |
| 3,919,051 | A | 11/1975 | Koch et al. |
| 3,923,060 | A | 12/1975 | Ellinwood, Jr. |
| 3,926,760 | A | 12/1975 | Allen et al. |
| 3,949,388 | A | 4/1976 | Fuller |
| 3,972,320 | A | 8/1976 | Kalman |
| 3,979,274 | A | 9/1976 | Newman |
| 4,003,379 | A | 1/1977 | Ellinwood, Jr. |

(Continued)

FOREIGN PATENT DOCUMENTS

| | | |
|---|---|---|
| AU | 2003/259741 | 2/2004 |
| CA | 2495648 | 2/2004 |

(Continued)

OTHER PUBLICATIONS

Li et al. "In vivo relase from a drug delivery MEMS device" Journal of Controlloed Release 100 (2004) 21 1-219 Aug. 18, 2004 Elsevier B.V.*

(Continued)

*Primary Examiner* — Sherief Badawi
*Assistant Examiner* — Berhanu Mitiku
(74) *Attorney, Agent, or Firm* — Jackson & Co., LLP

(57) ABSTRACT

Methods and devices for statistical determination of medication dosage level such as bolus amount based on contextual information are provided.

41 Claims, 7 Drawing Sheets

(56) References Cited

U.S. PATENT DOCUMENTS 4,008,717 A 2/1977 Kowarski
4,016,866 A 4/1977 Lawton
4,036,749 A 7/1977 Anderson
4,055,175 A 10/1977 Clemens et al.
4,059,406 A 11/1977 Fleet
4,076,596 A 2/1978 Connery et al.
4,098,574 A 7/1978 Dappen
4,100,048 A 7/1978 Pompei et al.
4,129,128 A 12/1978 McFarlane
4,151,845 A 5/1979 Clemens
4,154,231 A 5/1979 Russell
4,168,205 A 9/1979 Danninger et al.
4,172,770 A 10/1979 Semersky et al.
4,178,916 A 12/1979 McNamara
4,206,755 A 6/1980 Klein
4,224,125 A 9/1980 Nakamura et al.
4,240,438 A 12/1980 Updike et al.
4,240,889 A 12/1980 Yoda et al.
4,245,634 A 1/1981 Albisser et al.
4,247,297 A 1/1981 Berti et al.
4,271,449 A 6/1981 Grogan
4,318,784 A 3/1982 Higgins et al.
4,327,725 A 5/1982 Cortese et al.
4,331,869 A 5/1982 Rollo
4,340,458 A 7/1982 Lerner et al.
4,344,438 A 8/1982 Schultz
4,349,728 A 9/1982 Phillips et al.
4,352,960 A 10/1982 Dormer et al.
4,356,074 A 10/1982 Johnson
4,365,637 A 12/1982 Johnson
4,366,033 A 12/1982 Richter et al.
4,375,399 A 3/1983 Havas et al.
4,384,586 A 5/1983 Christiansen
4,390,621 A 6/1983 Bauer
4,392,933 A 7/1983 Nakamura et al.
4,401,122 A 8/1983 Clark, Jr.
4,404,066 A 9/1983 Johnson
4,407,959 A 10/1983 Tsuji et al.
4,417,588 A 11/1983 Houghton et al.
4,418,148 A 11/1983 Oberhardt
4,420,564 A 12/1983 Tsuji et al.
4,425,920 A 1/1984 Bourland et al.
4,427,004 A 1/1984 Miller et al.
4,427,770 A 1/1984 Chen et al.
4,431,004 A 2/1984 Bessman et al.
4,436,094 A 3/1984 Cerami
4,440,175 A 4/1984 Wilkins
4,444,892 A 4/1984 Malmros
4,450,842 A 5/1984 Zick et al.
4,458,686 A 7/1984 Clark, Jr.
4,461,691 A 7/1984 Frank
4,464,170 A 8/1984 Clemens et al.
4,467,811 A 8/1984 Clark, Jr.
4,469,110 A 9/1984 Slama
4,477,314 A 10/1984 Richter et al.
4,478,976 A 10/1984 Goertz et al.
4,483,924 A 11/1984 Tsuji et al.
4,484,987 A 11/1984 Gough
4,494,950 A 1/1985 Fischell
4,509,531 A 4/1985 Ward
4,512,348 A 4/1985 Uchigaki et al.
4,522,690 A 6/1985 Venkatsetty
4,524,114 A 6/1985 Samuels et al.
4,526,661 A 7/1985 Steckhan et al.
4,527,240 A 7/1985 Kvitash
4,534,356 A 8/1985 Papadakis
4,538,616 A 9/1985 Rogoff
4,543,955 A 10/1985 Schroeppel
4,545,382 A 10/1985 Higgins et al.
4,552,840 A 11/1985 Riffer
4,560,534 A 12/1985 Kung et al.
4,569,589 A 2/1986 Neufeld
4,571,292 A 2/1986 Liu et al.
4,573,994 A 3/1986 Fischell et al.
4,581,336 A 4/1986 Malloy et al.
4,595,011 A 6/1986 Phillips
4,595,479 A 6/1986 Kimura et al.
4,601,707 A 7/1986 Albisser et al.
4,619,754 A 10/1986 Niki et al.
4,619,793 A 10/1986 Lee
4,627,445 A 12/1986 Garcia et al.
4,627,908 A 12/1986 Miller
4,633,878 A 1/1987 Bombardien
4,633,881 A 1/1987 Moore et al.
4,637,403 A 1/1987 Garcia et al.
4,648,408 A 3/1987 Hutcheson et al.
4,650,547 A 3/1987 Gough
4,653,513 A 3/1987 Dombrowski
4,654,197 A 3/1987 Lilja et al.
4,655,880 A 4/1987 Liu
4,655,885 A 4/1987 Hill et al.
4,658,463 A 4/1987 Sugita et al.
4,671,288 A 6/1987 Gough
4,674,652 A 6/1987 Aten et al.
4,679,562 A 7/1987 Luksha
4,680,268 A 7/1987 Clark, Jr.
4,682,602 A 7/1987 Prohaska
4,684,537 A 8/1987 Graetzel et al.
4,685,463 A 8/1987 Williams
4,685,903 A 8/1987 Cable et al.
4,686,624 A 8/1987 Blum et al.
4,703,756 A 11/1987 Gough et al.
4,711,245 A 12/1987 Higgins et al.
4,717,673 A 1/1988 Wrighton et al.
4,721,601 A 1/1988 Wrighton et al.
4,721,677 A 1/1988 Clark, Jr.
4,726,378 A 2/1988 Kaplan
4,726,716 A 2/1988 McGuire
4,731,726 A 3/1988 Allen, III
4,749,985 A 6/1988 Corsberg
4,750,496 A 6/1988 Reinhart et al.
4,757,022 A 7/1988 Shults et al.
4,758,323 A 7/1988 Davis et al.
4,759,371 A 7/1988 Franetzki
4,759,828 A 7/1988 Young et al.
4,764,416 A 8/1988 Ueyama et al.
4,776,944 A 10/1988 Janata et al.
4,777,953 A 10/1988 Ash et al.
4,779,618 A 10/1988 Mund et al.
4,781,798 A 11/1988 Gough
4,784,736 A 11/1988 Lonsdale et al.
4,795,707 A 1/1989 Niiyama et al.
4,796,634 A 1/1989 Huntsman et al.
4,803,625 A 2/1989 Fu et al.
4,805,624 A 2/1989 Yao et al.
4,813,424 A 3/1989 Wilkins
4,815,469 A 3/1989 Cohen et al.
4,820,399 A 4/1989 Senda et al.
4,822,337 A 4/1989 Newhouse et al.
4,830,959 A 5/1989 McNeil et al.
4,832,797 A 5/1989 Vadgama et al.
4,835,372 A 5/1989 Gombrich et al.
RE32,947 E 6/1989 Dormer et al.
4,837,049 A 6/1989 Byers et al.
4,840,893 A 6/1989 Hill et al.
RE32,974 E 7/1989 Porat et al.
4,844,076 A 7/1989 Lesho et al.
4,845,035 A 7/1989 Fanta et al.
4,847,785 A 7/1989 Stephens
4,848,351 A 7/1989 Finch
4,854,322 A 8/1989 Ash et al.
4,856,340 A 8/1989 Garrison
4,857,713 A 8/1989 Brown
4,858,617 A 8/1989 Sanders
4,870,561 A 9/1989 Love et al.
4,871,351 A 10/1989 Feingold
4,871,440 A 10/1989 Nagata et al.
4,874,499 A 10/1989 Smith et al.
4,874,500 A 10/1989 Madou et al.
4,890,620 A 1/1990 Gough
4,890,621 A 1/1990 Hakky
4,894,137 A 1/1990 Takizawa et al.
4,897,162 A 1/1990 Lewandowski et al.
4,897,173 A 1/1990 Nankai et al.

(56) References Cited

U.S. PATENT DOCUMENTS 4,899,839 A 2/1990 Dessertine et al.
4,909,908 A 3/1990 Ross et al.
4,911,794 A 3/1990 Parce et al.
4,917,800 A 4/1990 Lonsdale et al.
4,919,141 A 4/1990 Zier et al.
4,919,767 A 4/1990 Vadgama et al.
4,920,969 A 5/1990 Suzuki
4,920,977 A 5/1990 Haynes
4,923,586 A 5/1990 Katayama et al.
4,925,268 A 5/1990 Iyer et al.
4,927,516 A 5/1990 Yamaguchi et al.
4,931,795 A 6/1990 Gord
4,934,369 A 6/1990 Maxwell
4,935,105 A 6/1990 Churchouse
4,935,345 A 6/1990 Guilbeau et al.
4,936,956 A 6/1990 Wrighton
4,938,860 A 7/1990 Wogoman
4,942,127 A 7/1990 Wada et al.
4,944,299 A 7/1990 Silvian
4,945,045 A 7/1990 Forrest et al.
4,950,378 A 8/1990 Nagata
4,953,552 A 9/1990 DeMarzo
4,954,129 A 9/1990 Giuliani et al.
4,957,115 A 9/1990 Selker
4,958,632 A 9/1990 Duggan
4,968,400 A 11/1990 Shimomura et al.
4,969,468 A 11/1990 Byers et al.
4,970,145 A 11/1990 Bennetto et al.
4,974,929 A 12/1990 Curry
4,979,509 A 12/1990 Hakky
4,986,271 A 1/1991 Wilkins
4,990,845 A 2/1991 Gord
4,991,582 A 2/1991 Byers et al.
4,994,068 A 2/1991 Hufnagle
4,994,167 A 2/1991 Shults et al.
4,995,402 A 2/1991 Smith et al.
5,000,180 A 3/1991 Kuypers et al.
5,001,054 A 3/1991 Wagner
5,002,054 A 3/1991 Ash et al.
5,007,427 A 4/1991 Suzuki et al.
5,016,172 A 5/1991 Dessertine
5,016,201 A 5/1991 Bryan et al.
5,019,974 A 5/1991 Beckers
5,034,192 A 7/1991 Wrighton et al.
5,035,860 A 7/1991 Kleingeld et al.
5,036,860 A 8/1991 Leigh et al.
5,036,861 A 8/1991 Sembrowich et al.
5,037,527 A 8/1991 Hayashi et al.
5,049,487 A 9/1991 Phillips et al.
5,050,612 A 9/1991 Matsumura
5,055,171 A 10/1991 Peck
5,058,592 A 10/1991 Whisler
5,063,081 A 11/1991 Cozzette et al.
5,068,536 A 11/1991 Rosenthal
5,070,535 A 12/1991 Hochmair et al.
5,073,500 A 12/1991 Saito et al.
5,077,476 A 12/1991 Rosenthal
5,078,854 A 1/1992 Burgess et al.
5,082,550 A 1/1992 Rishpon et al.
5,082,786 A 1/1992 Nakamoto
5,084,828 A 1/1992 Kaufman et al.
5,089,112 A 2/1992 Skotheim et al.
5,094,951 A 3/1992 Rosenberg
5,095,904 A 3/1992 Seligman et al.
5,096,560 A 3/1992 Takai et al.
5,096,836 A 3/1992 Macho et al.
5,097,834 A 3/1992 Skrabal
5,101,814 A 4/1992 Palti
5,106,365 A 4/1992 Hernandez
5,108,564 A 4/1992 Szuminsky et al.
5,109,850 A 5/1992 Blanco et al.
5,111,539 A 5/1992 Hiruta et al.
5,111,818 A 5/1992 Suzuki et al.
5,114,678 A 5/1992 Crawford et al.
5,120,420 A 6/1992 Nankai et al.
5,120,421 A 6/1992 Glass et al.
5,122,925 A 6/1992 Inpyn
5,126,034 A 6/1992 Carter et al.
5,126,247 A 6/1992 Palmer et al.
5,130,009 A 7/1992 Marsoner et al.
5,133,856 A 7/1992 Yamaguchi et al.
5,134,391 A 7/1992 Okada
5,135,003 A 8/1992 Souma
5,139,023 A 8/1992 Stanley et al.
5,140,393 A 8/1992 Hijikihigawa et al.
5,141,868 A 8/1992 Shanks et al.
5,161,532 A 11/1992 Joseph
5,165,407 A 11/1992 Wilson et al.
5,168,046 A 12/1992 Hamamoto et al.
5,174,291 A 12/1992 Schoonen et al.
5,176,644 A 1/1993 Srisathapat et al.
5,176,662 A 1/1993 Bartholomew et al.
5,182,707 A 1/1993 Cooper et al.
5,184,359 A 2/1993 Tsukamura et al.
5,185,256 A 2/1993 Nankai et al.
5,190,041 A 3/1993 Palti
5,192,415 A 3/1993 Yoshioka et al.
5,192,416 A 3/1993 Wang et al.
5,193,539 A 3/1993 Schulman et al.
5,193,540 A 3/1993 Schulman et al.
5,197,322 A 3/1993 Indravudh
5,198,367 A 3/1993 Aizawa et al.
5,200,051 A 4/1993 Cozzette et al.
5,202,261 A 4/1993 Musho et al.
5,205,920 A 4/1993 Oyama et al.
5,206,145 A 4/1993 Cattell
5,208,154 A 5/1993 Weaver et al.
5,209,229 A 5/1993 Gilli
5,215,887 A 6/1993 Saito
5,216,597 A 6/1993 Beckers
5,217,442 A 6/1993 Davis
5,217,595 A 6/1993 Smith et al.
5,227,042 A 7/1993 Zawodzinski et al.
5,229,282 A 7/1993 Yoshioka et al.
5,231,988 A 8/1993 Wernicke et al.
5,236,143 A 8/1993 Dragon
5,237,993 A 8/1993 Skrabal
5,246,867 A 9/1993 Lakowicz et al.
5,250,439 A 10/1993 Musho et al.
5,251,126 A 10/1993 Kahn et al.
5,257,971 A 11/1993 Lord et al.
5,257,980 A 11/1993 Van Antwerp et al.
5,261,401 A 11/1993 Baker et al.
5,262,035 A 11/1993 Gregg et al.
5,262,305 A 11/1993 Heller et al.
5,264,103 A 11/1993 Yoshioka et al.
5,264,104 A 11/1993 Gregg et al.
5,264,105 A 11/1993 Gregg et al.
5,264,106 A 11/1993 McAleer et al.
5,265,888 A 11/1993 Yamamoto et al.
5,266,179 A 11/1993 Nankai et al.
5,269,212 A 12/1993 Peters et al.
5,271,815 A 12/1993 Wong
5,272,060 A 12/1993 Hamamoto et al.
5,275,159 A 1/1994 Griebel
5,278,079 A 1/1994 Gubinski et al.
5,279,294 A 1/1994 Anderson et al.
5,282,950 A 2/1994 Dietze et al.
5,284,156 A 2/1994 Schramm et al.
5,285,792 A 2/1994 Sjoquist et al.
5,286,362 A 2/1994 Hoenes et al.
5,286,364 A 2/1994 Yacynych et al.
5,288,636 A 2/1994 Pollmann et al.
5,291,887 A 3/1994 Stanley et al.
5,293,546 A 3/1994 Tadros et al.
5,293,877 A 3/1994 O'Hara et al.
5,299,571 A 4/1994 Mastrototaro
5,304,468 A 4/1994 Phillips et al.
5,307,263 A 4/1994 Brown
5,309,919 A 5/1994 Snell et al.
5,310,885 A 5/1994 Maier et al.
5,320,098 A 6/1994 Davidson
5,320,725 A 6/1994 Gregg et al.
5,322,063 A 6/1994 Allen et al.

(56) References Cited

U.S. PATENT DOCUMENTS 5,324,303 A 6/1994 Strong et al.
5,324,316 A 6/1994 Schulman et al.
5,326,449 A 7/1994 Cunningham
5,337,258 A 8/1994 Dennis
5,337,747 A 8/1994 Neftel
5,340,722 A 8/1994 Wolfbeis et al.
5,342,789 A 8/1994 Chick et al.
5,352,348 A 10/1994 Young et al.
5,356,348 A 10/1994 Bellio et al.
5,356,786 A 10/1994 Heller et al.
5,358,514 A 10/1994 Schulman et al.
5,360,404 A 11/1994 Novacek et al.
5,364,797 A 11/1994 Olson et al.
5,366,609 A 11/1994 White et al.
5,368,028 A 11/1994 Palti
5,370,622 A 12/1994 Livingston et al.
5,371,687 A 12/1994 Holmes, II et al.
5,372,133 A 12/1994 Hogen Esch
5,372,427 A 12/1994 Padovani et al.
5,376,070 A 12/1994 Purvis et al.
5,376,251 A 12/1994 Kaneko et al.
5,377,258 A 12/1994 Bro
5,378,628 A 1/1995 Gratzel et al.
5,379,238 A 1/1995 Stark
5,380,422 A 1/1995 Negishis et al.
5,382,346 A 1/1995 Uenoyama et al.
5,384,547 A 1/1995 Lynk et al.
5,387,327 A 2/1995 Khan
5,390,671 A 2/1995 Lord et al.
5,391,250 A 2/1995 Cheney, II et al.
5,393,903 A 2/1995 Gratzel et al.
5,395,504 A 3/1995 Saurer et al.
5,399,823 A 3/1995 McCusker
5,400,782 A 3/1995 Beaubiah
5,408,999 A 4/1995 Singh et al.
5,410,471 A 4/1995 Alyfuku et al.
5,410,474 A 4/1995 Fox
5,411,647 A 5/1995 Johnson et al.
5,413,690 A 5/1995 Kost et al.
5,422,246 A 6/1995 Koopal et al.
5,429,602 A 7/1995 Hauser
5,431,160 A 7/1995 Wilkins
5,431,691 A 7/1995 Snell et al.
5,431,921 A 7/1995 Thombre
5,433,710 A 7/1995 Van Antwerp et al.
5,437,973 A 8/1995 Vadgama et al.
5,437,999 A 8/1995 Dieboid et al.
5,445,611 A 8/1995 Eppstein et al.
5,445,920 A 8/1995 Saito
5,456,692 A 10/1995 Smith, Jr. et al.
5,456,940 A 10/1995 Funderburk
5,458,140 A 10/1995 Eppstein et al.
5,460,618 A 10/1995 Harreld
5,462,525 A 10/1995 Srisathapat et al.
5,462,645 A 10/1995 Albery et al.
5,466,218 A 11/1995 Srisathapat et al.
5,469,846 A 11/1995 Khan
5,472,317 A 12/1995 Field et al.
5,476,460 A 12/1995 Montalvo
5,477,855 A 12/1995 Schindler et al.
5,482,473 A 1/1996 Lord et al.
5,484,404 A 1/1996 Schulman et al.
5,487,751 A 1/1996 Radons et al.
5,491,474 A 2/1996 Suni et al.
5,494,562 A 2/1996 Maley et al.
5,496,453 A 3/1996 Uenoyama et al.
5,497,772 A 3/1996 Schulman et al.
5,501,956 A 3/1996 Wada et al.
5,505,709 A 4/1996 Funderburk
5,505,713 A 4/1996 Van Antwerp et al.
5,507,288 A 4/1996 Bocker et al.
5,508,171 A 4/1996 Walling et al.
5,509,410 A 4/1996 Hill et al.
5,514,103 A 5/1996 Srisathapat et al.
5,514,253 A 5/1996 Davis et al.
5,514,718 A 5/1996 Lewis et al.
5,518,006 A 5/1996 Mawhirt et al.
5,520,787 A 5/1996 Hanagan et al.
5,522,865 A 6/1996 Schulman et al.
5,525,511 A 6/1996 D'Costa
5,526,120 A 6/1996 Jina et al.
5,527,307 A 6/1996 Srisathapat et al.
5,529,676 A 6/1996 Maley et al.
5,531,878 A 7/1996 Vadgama et al.
5,538,511 A 7/1996 Van Antwerp et al.
5,545,152 A 8/1996 Funderburk et al.
5,545,191 A 8/1996 Mann et al.
5,549,113 A 8/1996 Halleck et al.
5,549,115 A 8/1996 Morgan et al.
5,552,027 A 9/1996 Birkle et al.
5,552,997 A 9/1996 Massart
5,554,166 A 9/1996 Lange et al.
5,556,524 A 9/1996 Albers
5,560,357 A 10/1996 Faupei et al.
5,562,713 A 10/1996 Silvian
5,565,085 A 10/1996 Ikeda et al.
5,567,302 A 10/1996 Song et al.
5,568,806 A 10/1996 Cheney, II et al.
5,569,186 A 10/1996 Lord et al.
5,569,212 A 10/1996 Brown
5,573,647 A 11/1996 Maley et al.
5,575,895 A 11/1996 Ikeda et al.
5,580,527 A 12/1996 Bell et al.
5,580,794 A 12/1996 Allen
5,582,184 A 12/1996 Erickson et al.
5,582,697 A 12/1996 Ikeda et al.
5,582,698 A 12/1996 Flaherty et al.
5,584,813 A 12/1996 Livingston et al.
5,586,553 A 12/1996 Halli et al.
5,589,326 A 12/1996 Deng et al.
5,593,852 A 1/1997 Heller et al.
5,594,906 A 1/1997 Holmes, II et al.
5,596,150 A 1/1997 Arndy et al.
5,596,994 A 1/1997 Bro
5,601,435 A 2/1997 Quy
5,601,694 A 2/1997 Maley et al.
5,605,152 A 2/1997 Slate et al.
5,609,575 A 3/1997 Larson et al.
5,611,900 A 3/1997 Worden et al.
5,615,671 A 4/1997 Schoonen et al.
5,616,222 A 4/1997 Maley et al.
5,617,851 A 4/1997 Lipkovker
5,623,925 A 4/1997 Swenson et al.
5,628,309 A 5/1997 Brown
5,628,310 A 5/1997 Rao et al.
5,628,890 A 5/1997 Carter et al.
5,629,981 A 5/1997 Nerlikar
5,637,095 A 6/1997 Nason et al.
5,640,764 A 6/1997 Strojnik
5,640,954 A 6/1997 Pfeiffer et al.
5,643,212 A 7/1997 Coutre et al.
5,647,853 A 7/1997 Feldmann et al.
5,650,062 A 7/1997 Ikeda et al.
5,651,767 A 7/1997 Schulman et al.
5,651,869 A 7/1997 Yoshioka et al.
5,653,239 A 8/1997 Pompei et al.
5,660,163 A 8/1997 Schulman et al.
5,665,065 A 9/1997 Colman et al.
5,665,222 A 9/1997 Heller et al.
5,667,983 A 9/1997 Abel et al.
5,670,031 A 9/1997 Hintsche et al.
5,678,571 A 10/1997 Brown
5,679,690 A 10/1997 Andre et al.
5,680,858 A 10/1997 Hansen et al.
5,682,233 A 10/1997 Brinda
5,686,717 A 11/1997 Knowles et al.
5,695,623 A 12/1997 Michel et al.
5,695,949 A 12/1997 Galen et al.
5,701,894 A 12/1997 Cherry et al.
5,704,922 A 1/1998 Brown
5,707,502 A 1/1998 McCaffrey et al.
5,708,247 A 1/1998 McAleer et al.
5,710,630 A 1/1998 Essenpreis et al.
5,711,001 A 1/1998 Bussan et al.

(56) References Cited

U.S. PATENT DOCUMENTS 5,711,297 A 1/1998 Iliff
5,711,861 A 1/1998 Ward et al.
5,711,862 A 1/1998 Sakoda et al.
5,711,868 A 1/1998 Maley et al.
5,718,234 A 2/1998 Warden et al.
5,720,733 A 2/1998 Brown
5,720,862 A 2/1998 Hamamoto et al.
5,721,783 A 2/1998 Anderson
5,722,397 A 3/1998 Eppstein
5,727,548 A 3/1998 Hill et al.
5,730,124 A 3/1998 Yamauchi
5,730,654 A 3/1998 Brown
5,735,273 A 4/1998 Kurnik et al.
5,735,285 A 4/1998 Albert et al.
5,741,211 A 4/1998 Renirie et al.
5,741,688 A 4/1998 Oxenboll et al.
5,746,217 A 5/1998 Erickson et al.
5,750,926 A 5/1998 Schulman et al.
5,768,591 A 6/1998 Robinson
5,770,028 A 6/1998 Maley et al.
5,771,001 A 6/1998 Cobb
5,771,890 A 6/1998 Tamada
5,772,586 A 6/1998 Heinonen et al.
5,777,060 A 7/1998 Van Antwerp
5,779,665 A 7/1998 Mastrototaro et al.
5,782,814 A 7/1998 Brown et al.
5,785,681 A 7/1998 Indravudh
5,786,439 A 7/1998 Van Antwerp et al.
5,786,584 A 7/1998 Button et al.
5,788,678 A 8/1998 Van Antwerp
5,791,344 A 8/1998 Schulman et al.
5,792,117 A 8/1998 Brown
5,800,420 A 9/1998 Gross et al.
5,804,048 A 9/1998 Wong et al.
5,807,315 A 9/1998 Van Antwerp et al.
5,807,375 A 9/1998 Gross et al.
5,814,599 A 9/1998 Mitragotri et al.
5,820,551 A 10/1998 Hill et al.
5,820,570 A 10/1998 Erickson et al.
5,820,622 A 10/1998 Gross et al.
5,822,715 A 10/1998 Worthington et al.
5,825,488 A 10/1998 Kohl et al.
5,827,179 A 10/1998 Lichter et al.
5,827,183 A 10/1998 Kurnik et al.
5,827,184 A 10/1998 Netherly et al.
5,828,943 A 10/1998 Brown
5,830,341 A 11/1998 Gilmartin
5,832,448 A 11/1998 Brown
5,834,224 A 11/1998 Ruger et al.
5,837,454 A 11/1998 Cozzette et al.
5,837,546 A 11/1998 Allen et al.
5,840,020 A 11/1998 Heinonen et al.
5,842,983 A 12/1998 Abel et al.
5,843,140 A 12/1998 Strojnik
5,846,702 A 12/1998 Deng et al.
5,846,744 A 12/1998 Athey et al.
5,851,197 A 12/1998 Marano et al.
5,854,078 A 12/1998 Asher et al.
5,854,189 A 12/1998 Kruse et al.
5,857,967 A 1/1999 Frid et al.
5,857,983 A 1/1999 Douglas et al.
5,860,917 A 1/1999 Comanor et al.
5,872,713 A 2/1999 Douglas et al.
5,876,484 A 3/1999 Raskin et al.
5,879,163 A 3/1999 Brown et al.
5,879,311 A 3/1999 Duchon et al.
5,880,829 A 3/1999 Kauhaniemi et al.
5,882,494 A 3/1999 Van Antwerp
5,885,211 A 3/1999 Eppstein et al.
5,887,133 A 3/1999 Brown et al.
5,897,493 A 4/1999 Brown
5,898,025 A 4/1999 Burg et al.
5,899,855 A 5/1999 Brown
5,913,310 A 6/1999 Brown
5,917,346 A 6/1999 Gord
5,918,603 A 7/1999 Brown
5,925,021 A 7/1999 Castellano et al.
5,931,791 A 8/1999 Saltzstein et al.
5,933,136 A 8/1999 Brown
5,940,801 A 8/1999 Brown
5,942,979 A 8/1999 Luppino
5,945,345 A 8/1999 Blatt et al.
5,947,921 A 9/1999 Johnson et al.
5,948,512 A 9/1999 Kubota et al.
5,950,632 A 9/1999 Reber et al.
5,951,300 A 9/1999 Brown
5,951,492 A 9/1999 Douglas et al.
5,951,521 A 9/1999 Mastrototaro et al.
5,951,836 A 9/1999 McAleer et al.
5,954,643 A 9/1999 Van Antwerp
5,954,685 A 9/1999 Tierny
5,954,700 A 9/1999 Kovelman
5,956,501 A 9/1999 Brown
5,957,854 A 9/1999 Besson et al.
5,957,890 A 9/1999 Mann et al.
5,957,958 A 9/1999 Schulman et al.
5,960,403 A 9/1999 Brown
5,961,451 A 10/1999 Reber et al.
5,964,993 A 10/1999 Blubaugh, Jr. et al.
5,965,380 A 10/1999 Heller et al.
5,968,839 A 10/1999 Blatt et al.
5,971,922 A 10/1999 Arita et al.
5,971,941 A 10/1999 Simons et al.
5,974,124 A 10/1999 Schlueter, Jr. et al.
5,977,476 A 11/1999 Guha et al.
5,981,294 A 11/1999 Blatt et al.
5,989,409 A 11/1999 Kurnik et al.
5,994,476 A 11/1999 Shin et al.
5,995,860 A 11/1999 Sun et al.
5,997,476 A 12/1999 Brown
5,999,848 A 12/1999 Gord et al.
5,999,849 A 12/1999 Gord et al.
6,001,067 A 12/1999 Shults et al.
6,002,954 A 12/1999 Van Antwerp et al.
6,002,961 A 12/1999 Mitragotri et al.
6,004,441 A 12/1999 Fujiwara et al.
6,011,984 A 1/2000 Van Antwerp et al.
6,014,577 A 1/2000 Henning et al.
6,018,678 A 1/2000 Mitragotri et al.
6,023,629 A 2/2000 Tamada
6,024,699 A 2/2000 Surwit et al.
6,026,320 A 2/2000 Carlson et al.
6,027,459 A 2/2000 Shain et al.
6,027,692 A 2/2000 Galen et al.
6,032,059 A 2/2000 Henning et al.
6,032,199 A 2/2000 Lim et al.
6,033,866 A 3/2000 Guo et al.
6,035,237 A 3/2000 Schulman et al.
6,040,194 A 3/2000 Chick et al.
6,041,253 A 3/2000 Kost et al.
6,043,437 A 3/2000 Schulman et al.
6,049,727 A 4/2000 Crothall
6,056,718 A 5/2000 Funderburk et al.
6,063,459 A 5/2000 Velte
6,066,243 A 5/2000 Anderson et al.
6,067,474 A 5/2000 Schulman et al.
6,068,615 A 5/2000 Brown et al.
6,071,249 A 6/2000 Cunningham et al.
6,071,251 A 6/2000 Cunningham et al.
6,071,294 A 6/2000 Simons et al.
6,071,391 A 6/2000 Gotoh et al.
6,073,031 A 6/2000 Helstab et al.
6,081,736 A 6/2000 Colvin et al.
6,083,710 A 7/2000 Heller et al.
6,088,608 A 7/2000 Schulman et al.
6,091,975 A 7/2000 Daddona et al.
6,091,976 A 7/2000 Pfeiffer et al.
6,093,156 A 7/2000 Cunningham et al.
6,093,167 A 7/2000 Houben et al.
6,093,172 A 7/2000 Funderburk et al.
6,096,364 A 8/2000 Bok et al.
6,097,831 A 8/2000 Wieck et al.
6,099,484 A 8/2000 Douglas et al.
6,101,478 A 8/2000 Brown

(56) References Cited

U.S. PATENT DOCUMENTS

| | | | |
|---|---|---|---|
| 6,103,033 | A | 8/2000 | Say et al. |
| 6,106,780 | A | 8/2000 | Douglas et al. |
| 6,110,148 | A | 8/2000 | Brown et al. |
| 6,110,152 | A | 8/2000 | Kovelman |
| 6,113,578 | A | 9/2000 | Brown |
| 6,117,290 | A | 9/2000 | Say et al. |
| 6,119,028 | A | 9/2000 | Schulman et al. |
| 6,120,676 | A | 9/2000 | Heller et al. |
| 6,121,009 | A | 9/2000 | Heller et al. |
| 6,121,611 | A | 9/2000 | Lindsay et al. |
| 6,122,351 | A | 9/2000 | Schlueter, Jr. et al. |
| 6,125,978 | A | 10/2000 | Ando et al. |
| 6,134,461 | A | 10/2000 | Say et al. |
| 6,134,504 | A | 10/2000 | Douglas et al. |
| 6,139,718 | A | 10/2000 | Kurnik et al. |
| 6,141,573 | A | 10/2000 | Kurnik et al. |
| 6,142,939 | A | 11/2000 | Eppstein et al. |
| 6,143,164 | A | 11/2000 | Heller et al. |
| 6,144,837 | A | 11/2000 | Quy |
| 6,144,869 | A | 11/2000 | Berner et al. |
| 6,144,922 | A | 11/2000 | Douglas et al. |
| 6,148,094 | A | 11/2000 | Kinsella |
| 6,150,128 | A | 11/2000 | Uretsky |
| 6,151,586 | A | 11/2000 | Brown |
| 6,153,062 | A | 11/2000 | Saito et al. |
| 6,153,069 | A | 11/2000 | Pottgen et al. |
| 6,159,147 | A | 12/2000 | Lichter et al. |
| 6,161,095 | A | 12/2000 | Brown |
| 6,162,611 | A | 12/2000 | Heller et al. |
| 6,162,639 | A | 12/2000 | Douglas |
| 6,167,362 | A | 12/2000 | Brown et al. |
| 6,168,563 | B1 | 1/2001 | Brown |
| 6,170,318 | B1 | 1/2001 | Lewis |
| 6,175,752 | B1 | 1/2001 | Say et al. |
| 6,180,416 | B1 | 1/2001 | Kurnik et al. |
| 6,186,145 | B1 | 2/2001 | Brown |
| 6,192,891 | B1 | 2/2001 | Gravel et al. |
| 6,193,873 | B1 | 2/2001 | Ohara et al. |
| 6,196,970 | B1 | 3/2001 | Brown |
| 6,198,957 | B1 | 3/2001 | Green |
| 6,200,265 | B1 | 3/2001 | Walsh et al. |
| 6,201,979 | B1 | 3/2001 | Kurnik et al. |
| 6,201,980 | B1 | 3/2001 | Darrow et al. |
| 6,206,841 | B1 | 3/2001 | Cunningham et al. |
| 6,207,400 | B1 | 3/2001 | Kwon |
| 6,208,894 | B1 | 3/2001 | Schulman et al. |
| 6,210,272 | B1 | 4/2001 | Brown |
| 6,210,976 | B1 | 4/2001 | Sabbadini |
| 6,212,416 | B1 | 4/2001 | Ward et al. |
| 6,219,565 | B1 | 4/2001 | Cupp et al. |
| 6,219,574 | B1 | 4/2001 | Cormier et al. |
| 6,224,745 | B1 | 5/2001 | Baltruschat |
| 6,232,130 | B1 | 5/2001 | Wolf |
| 6,232,370 | B1 | 5/2001 | Kubota et al. |
| 6,233,471 | B1 | 5/2001 | Berner et al. |
| 6,233,539 | B1 | 5/2001 | Brown |
| 6,239,925 | B1 | 5/2001 | Ardrey et al. |
| 6,241,862 | B1 | 6/2001 | McAleer et al. |
| 6,246,330 | B1 | 6/2001 | Nielsen |
| 6,246,992 | B1 | 6/2001 | Brown |
| 6,248,065 | B1 | 6/2001 | Brown |
| 6,248,067 | B1 | 6/2001 | Causey, III et al. |
| 6,248,093 | B1 | 6/2001 | Moberg |
| 6,251,260 | B1 | 6/2001 | Heller et al. |
| 6,252,032 | B1 | 6/2001 | Van Antwerp et al. |
| 6,253,804 | B1 | 7/2001 | Safabash |
| 6,254,586 | B1 | 7/2001 | Mann et al. |
| 6,256,643 | B1 | 7/2001 | Cork et al. |
| 6,259,587 | B1 | 7/2001 | Sheldon et al. |
| 6,259,937 | B1 | 7/2001 | Schulman et al. |
| 6,260,022 | B1 | 7/2001 | Brown |
| 6,266,645 | B1 | 7/2001 | Simpson |
| 6,267,724 | B1 | 7/2001 | Taylor |
| 6,268,161 | B1 | 7/2001 | Han et al. |
| 6,270,445 | B1 | 8/2001 | Dean, Jr. et al. |
| 6,272,364 | B1 | 8/2001 | Kurnik |
| 6,275,717 | B1 | 8/2001 | Gross et al. |
| 6,280,416 | B1 | 8/2001 | Van Antwerp et al. |
| 6,280,587 | B1 | 8/2001 | Matsumoto |
| 6,281,006 | B1 | 8/2001 | Heller et al. |
| 6,283,943 | B1 | 9/2001 | Dy et al. |
| 6,284,126 | B1 | 9/2001 | Kurnik et al. |
| 6,284,478 | B1 | 9/2001 | Heller et al. |
| 6,293,925 | B1 | 9/2001 | Safabash et al. |
| 6,294,281 | B1 | 9/2001 | Heller |
| 6,295,463 | B1 | 9/2001 | Stenzler |
| 6,295,506 | B1 | 9/2001 | Heinonen et al. |
| 6,298,254 | B2 | 10/2001 | Tamada |
| 6,299,578 | B1 | 10/2001 | Kurnik et al. |
| 6,299,757 | B1 | 10/2001 | Feldman et al. |
| 6,301,499 | B1 | 10/2001 | Carlson et al. |
| 6,304,766 | B1 | 10/2001 | Colvin, Jr. et al. |
| 6,306,104 | B1 | 10/2001 | Cunningham et al. |
| 6,309,351 | B1 | 10/2001 | Kurnik et al. |
| 6,309,884 | B1 | 10/2001 | Cooper et al. |
| 6,315,721 | B2 | 11/2001 | Schulman et al. |
| 6,319,540 | B1 | 11/2001 | Van Antwerp et al. |
| 6,326,160 | B1 | 12/2001 | Dunn et al. |
| 6,329,161 | B1 | 12/2001 | Heller et al. |
| 6,329,929 | B1 | 12/2001 | Weijand et al. |
| 6,330,426 | B2 | 12/2001 | Brown et al. |
| 6,330,464 | B1 | 12/2001 | Colvin, Jr. et al. |
| 6,331,518 | B2 | 12/2001 | Hemm et al. |
| 6,334,778 | B1 | 1/2002 | Brown |
| 6,336,900 | B1 | 1/2002 | Alleckson et al. |
| 6,338,790 | B1 | 1/2002 | Feldman et al. |
| 6,340,421 | B1 | 1/2002 | Vachon et al. |
| 6,341,232 | B1 | 1/2002 | Conn et al. |
| 6,356,776 | B1 | 3/2002 | Berner et al. |
| 6,360,888 | B1 | 3/2002 | McIvor et al. |
| 6,366,793 | B1 | 4/2002 | Bell et al. |
| 6,366,794 | B1 | 4/2002 | Moussy et al. |
| 6,368,141 | B1 | 4/2002 | Van Antwerp et al. |
| 6,368,274 | B1 | 4/2002 | Van Antwerp et al. |
| 6,370,410 | B2 | 4/2002 | Kurnik et al. |
| 6,377,828 | B1 | 4/2002 | Chaiken et al. |
| 6,379,301 | B1 | 4/2002 | Worthington et al. |
| 6,383,767 | B1 | 5/2002 | Polak |
| 6,387,048 | B1 | 5/2002 | Schulman et al. |
| 6,391,643 | B1 | 5/2002 | Chen et al. |
| 6,393,318 | B1 | 5/2002 | Conn et al. |
| 6,398,562 | B1 | 6/2002 | Butler et al. |
| 6,405,066 | B1 | 6/2002 | Essenpreis et al. |
| 6,413,393 | B1 | 7/2002 | Van Antwerp et al. |
| 6,418,332 | B1 | 7/2002 | Mastrototaro et al. |
| 6,424,847 | B1 | 7/2002 | Mastrototaro et al. |
| 6,427,088 | B1 | 7/2002 | Bowman, IV et al. |
| 6,434,409 | B1 | 8/2002 | Pfeiffer et al. |
| 6,438,414 | B1 | 8/2002 | Conn et al. |
| 6,440,068 | B1 | 8/2002 | Brown et al. |
| 6,442,637 | B1 | 8/2002 | Hawkins et al. |
| 6,443,942 | B2 | 9/2002 | Van Antwerp et al. |
| 6,454,710 | B1 | 9/2002 | Ballerstadt et al. |
| 6,462,162 | B2 | 10/2002 | Van Antwerp et al. |
| 6,464,848 | B1 | 10/2002 | Matsumoto |
| 6,466,810 | B1 | 10/2002 | Ward et al. |
| 6,468,222 | B1 | 10/2002 | Mault et al. |
| 6,471,689 | B1 | 10/2002 | Joseph et al. |
| 6,472,122 | B1 | 10/2002 | Schulman et al. |
| 6,475,750 | B1 | 11/2002 | Han et al. |
| 6,477,395 | B2 | 11/2002 | Schulman et al. |
| 6,478,736 | B1 | 11/2002 | Mault |
| 6,480,730 | B2 | 11/2002 | Darrow et al. |
| 6,482,156 | B2 | 11/2002 | Iliff |
| 6,482,158 | B2 | 11/2002 | Mault |
| 6,482,604 | B2 | 11/2002 | Kwon |
| 6,484,045 | B1 | 11/2002 | Holker et al. |
| 6,484,046 | B1 | 11/2002 | Say et al. |
| 6,485,138 | B1 | 11/2002 | Kubota et al. |
| 6,494,830 | B1 | 12/2002 | Wessel |
| 6,496,728 | B2 | 12/2002 | Li et al. |
| 6,505,059 | B1 | 1/2003 | Kollias et al. |
| 6,512,939 | B1 | 1/2003 | Colvin et al. |
| 6,513,532 | B2 | 2/2003 | Mault et al. |

(56) References Cited

U.S. PATENT DOCUMENTS

| | | | |
|---|---|---|---|
| 6,514,718 | B2 | 2/2003 | Heller et al. |
| 6,515,593 | B1 | 2/2003 | Stark et al. |
| 6,520,326 | B2 | 2/2003 | McIvor et al. |
| 6,529,755 | B2 | 3/2003 | Kurnik et al. |
| 6,529,772 | B2 | 3/2003 | Carlson et al. |
| 6,530,915 | B1 | 3/2003 | Eppstein et al. |
| 6,534,322 | B1 | 3/2003 | Sabbadini |
| 6,534,323 | B1 | 3/2003 | Sabbadini |
| 6,535,753 | B1 | 3/2003 | Raskas |
| 6,537,243 | B1 | 3/2003 | Henning et al. |
| 6,540,675 | B2 | 4/2003 | Aceti et al. |
| 6,544,212 | B2 | 4/2003 | Galley et al. |
| 6,546,269 | B1 | 4/2003 | Kurnik |
| 6,549,796 | B2 | 4/2003 | Sohrab |
| 6,551,276 | B1 | 4/2003 | Mann et al. |
| 6,551,494 | B1 | 4/2003 | Heller et al. |
| 6,553,244 | B2 | 4/2003 | Lesho et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,565,509 | B1 | 5/2003 | Say et al. |
| 6,571,128 | B2 | 5/2003 | Lebel et al. |
| 6,571,200 | B1 | 5/2003 | Mault |
| 6,572,545 | B2 | 6/2003 | Knobbe et al. |
| 6,576,101 | B1 | 6/2003 | Heller et al. |
| 6,576,117 | B1 | 6/2003 | Iketaki et al. |
| 6,577,899 | B2 | 6/2003 | Lebel et al. |
| 6,579,498 | B1 | 6/2003 | Eglise |
| 6,579,690 | B1 | 6/2003 | Bonnecaze et al. |
| 6,584,335 | B1 | 6/2003 | Haar et al. |
| 6,585,644 | B2 | 7/2003 | Lebel et al. |
| 6,587,705 | B1 | 7/2003 | Kim et al. |
| 6,587,995 | B1 | 7/2003 | Duboc et al. |
| 6,591,125 | B1 | 7/2003 | Buse et al. |
| 6,591,126 | B2 | 7/2003 | Roeper et al. |
| 6,594,514 | B2 | 7/2003 | Berner et al. |
| 6,595,919 | B2 | 7/2003 | Berner et al. |
| 6,595,929 | B2 | 7/2003 | Stivoric et al. |
| 6,600,997 | B2 | 7/2003 | Deweese et al. |
| 6,602,678 | B2 | 8/2003 | Kwon et al. |
| 6,602,909 | B1 | 8/2003 | Jarowski |
| 6,605,200 | B1 | 8/2003 | Mao et al. |
| 6,605,201 | B1 | 8/2003 | Mao et al. |
| 6,607,509 | B2 | 8/2003 | Bobroff et al. |
| 6,610,012 | B2 | 8/2003 | Mault |
| 6,612,306 | B1 | 9/2003 | Mault |
| 6,615,078 | B1 | 9/2003 | Burson et al. |
| 6,618,603 | B2 | 9/2003 | Varalli et al. |
| 6,620,106 | B2 | 9/2003 | Mault |
| 6,627,058 | B1 | 9/2003 | Chan |
| 6,629,934 | B2 | 10/2003 | Mault et al. |
| 6,633,772 | B2 | 10/2003 | Ford et al. |
| 6,635,014 | B2 | 10/2003 | Starkweather et al. |
| 6,641,533 | B2 | 11/2003 | Causey, III et al. |
| 6,642,015 | B2 | 11/2003 | Vachon et al. |
| 6,645,142 | B2 | 11/2003 | Braig et al. |
| 6,648,821 | B2 | 11/2003 | Lebel et al. |
| 6,653,091 | B1 | 11/2003 | Dunn et al. |
| 6,654,625 | B1 | 11/2003 | Say et al. |
| 6,656,114 | B1 * | 12/2003 | Poulsen et al. ................ 600/300 |
| 6,658,396 | B1 * | 12/2003 | Tang et al. ...................... 706/17 |
| 6,659,948 | B2 | 12/2003 | Lebel et al. |
| 6,668,196 | B1 | 12/2003 | Villegas et al. |
| 6,671,554 | B2 | 12/2003 | Gibson et al. |
| 6,673,625 | B2 | 1/2004 | Satcher, Jr. et al. |
| 6,675,030 | B2 | 1/2004 | Ciuczak et al. |
| 6,682,938 | B1 | 1/2004 | Satcher, Jr. et al. |
| 6,683,040 | B2 | 1/2004 | Bragulla et al. |
| 6,687,522 | B2 | 2/2004 | Tamada |
| 6,687,546 | B2 | 2/2004 | Lebel et al. |
| 6,689,056 | B1 | 2/2004 | Kilcoyne et al. |
| 6,693,069 | B2 | 2/2004 | Korber et al. |
| 6,694,158 | B2 | 2/2004 | Polak |
| 6,694,191 | B2 | 2/2004 | Starkweather et al. |
| 6,695,860 | B1 | 2/2004 | Ward et al. |
| 6,702,857 | B2 | 3/2004 | Brauker et al. |
| 6,704,587 | B1 | 3/2004 | Kumar et al. |
| 6,711,423 | B2 | 3/2004 | Colvin, Jr. |
| 6,723,046 | B2 | 4/2004 | Lichtenstein et al. |
| 6,728,560 | B2 | 4/2004 | Kollias et al. |
| 6,731,976 | B2 | 5/2004 | Penn et al. |
| 6,733,446 | B2 | 5/2004 | Lebel et al. |
| 6,734,162 | B2 | 5/2004 | Van Antwerp et al. |
| 6,736,777 | B2 | 5/2004 | Kim et al. |
| 6,736,797 | B1 | 5/2004 | Larsen et al. |
| 6,737,401 | B2 | 5/2004 | Kim et al. |
| 6,738,654 | B2 | 5/2004 | Sohrab |
| 6,740,075 | B2 | 5/2004 | Lebel et al. |
| 6,741,163 | B1 | 5/2004 | Roberts |
| 6,741,876 | B1 | 5/2004 | Scecina et al. |
| 6,741,877 | B1 | 5/2004 | Shults et al. |
| 6,744,350 | B2 | 6/2004 | Blomquist |
| 6,746,582 | B2 | 6/2004 | Heller et al. |
| 6,749,587 | B2 | 6/2004 | Flaherty |
| 6,750,311 | B1 | 6/2004 | Van Antwerp et al. |
| 6,758,810 | B2 | 7/2004 | Lebel et al. |
| 6,766,183 | B2 | 7/2004 | Walsh et al. |
| 6,766,201 | B2 | 7/2004 | Von Arx et al. |
| 6,768,425 | B2 | 7/2004 | Flaherty et al. |
| 6,770,030 | B1 | 8/2004 | Schaupp et al. |
| 6,770,729 | B2 | 8/2004 | Van Antwerp et al. |
| 6,771,995 | B2 | 8/2004 | Kurnik et al. |
| 6,773,563 | B2 | 8/2004 | Matsumoto |
| 6,780,297 | B2 | 8/2004 | Matsumoto et al. |
| 6,780,871 | B2 | 8/2004 | Glick et al. |
| 6,784,274 | B2 | 8/2004 | Van Antwerp et al. |
| 6,790,178 | B1 | 9/2004 | Mault et al. |
| 6,794,195 | B2 | 9/2004 | Colvin, Jr. |
| 6,800,451 | B2 | 10/2004 | Daniloff et al. |
| 6,804,544 | B2 | 10/2004 | Van Antwerp et al. |
| 6,809,507 | B2 | 10/2004 | Morgan et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,811,659 | B2 | 11/2004 | Vachon |
| 6,812,031 | B1 | 11/2004 | Carlsson |
| 6,813,519 | B2 | 11/2004 | Lebel et al. |
| 6,816,742 | B2 | 11/2004 | Kim et al. |
| 6,835,553 | B2 | 12/2004 | Han et al. |
| RE38,681 | E | 1/2005 | Kurnik et al. |
| 6,840,912 | B2 | 1/2005 | Kloepfer et al. |
| 6,844,023 | B2 | 1/2005 | Schulman et al. |
| 6,849,237 | B2 | 2/2005 | Housefield et al. |
| 6,850,790 | B2 | 2/2005 | Berner et al. |
| 6,852,104 | B2 | 2/2005 | Blomquist |
| 6,852,500 | B1 | 2/2005 | Hoss et al. |
| 6,852,694 | B2 | 2/2005 | Van Antwerp et al. |
| 6,853,854 | B1 | 2/2005 | Proniewicz et al. |
| 6,856,928 | B2 | 2/2005 | Harmon |
| 6,858,403 | B2 | 2/2005 | Han et al. |
| 6,862,465 | B2 | 3/2005 | Shults et al. |
| 6,862,466 | B2 | 3/2005 | Ackerman |
| 6,865,407 | B2 | 3/2005 | Kimball et al. |
| 6,872,200 | B2 | 3/2005 | Mann et al. |
| 6,873,268 | B2 | 3/2005 | Lebel et al. |
| 6,881,551 | B2 | 4/2005 | Heller et al. |
| 6,882,940 | B2 | 4/2005 | Potts et al. |
| 6,885,883 | B2 | 4/2005 | Parris et al. |
| 6,892,085 | B2 | 5/2005 | McIvor et al. |
| 6,895,263 | B2 | 5/2005 | Shin et al. |
| 6,895,265 | B2 | 5/2005 | Silver |
| 6,899,683 | B2 | 5/2005 | Mault et al. |
| 6,899,684 | B2 | 5/2005 | Mault et al. |
| 6,902,207 | B2 | 6/2005 | Lickliter |
| 6,902,905 | B2 | 6/2005 | Burson et al. |
| 6,904,301 | B2 | 6/2005 | Raskas |
| 6,907,127 | B1 | 6/2005 | Kravitz et al. |
| 6,915,147 | B2 | 7/2005 | Lebel et al. |

(56) References Cited

U.S. PATENT DOCUMENTS 6,918,874 B1 7/2005 Hatch et al.
6,922,578 B2 7/2005 Eppstein et al.
RE38,775 E 8/2005 Kurnik et al.
6,923,763 B1 8/2005 Kovatchev et al.
6,923,764 B2 8/2005 Aceti et al.
6,923,936 B2 8/2005 Swanson et al.
6,927,246 B2 8/2005 Noronha et al.
6,931,327 B2 8/2005 Goode, Jr. et al.
6,936,006 B2 8/2005 Sabra
6,936,029 B2 8/2005 Mann et al.
6,940,590 B2 9/2005 Colvin, Jr. et al.
6,941,163 B2 9/2005 Ford et al.
6,950,708 B2 9/2005 Bowman, IV et al.
6,952,603 B2 10/2005 Gerber et al.
6,954,673 B2 10/2005 Von Arx et al.
6,955,650 B2 10/2005 Mault et al.
6,957,102 B2 10/2005 Silver et al.
6,957,107 B2 10/2005 Rogers et al.
6,958,705 B2 10/2005 Lebel et al.
6,968,294 B2 11/2005 Gutta et al.
6,968,375 B1 11/2005 Brown
6,971,274 B2 12/2005 Olin
6,974,437 B2 12/2005 Lebel et al.
6,978,182 B2 12/2005 Mazar et al.
6,979,326 B2 12/2005 Mann et al.
6,983,176 B2 1/2006 Gardner et al.
6,990,366 B2 1/2006 Say et al.
6,991,096 B2 1/2006 Gottlieb et al.
6,997,907 B2 2/2006 Safabash et al.
6,997,920 B2 2/2006 Mann et al.
6,998,247 B2 2/2006 Monfre et al.
6,999,810 B2 2/2006 Berner et al.
7,003,336 B2 2/2006 Holker et al.
7,003,340 B2 2/2006 Say et al.
7,003,341 B2 2/2006 Say et al.
7,004,901 B2 2/2006 Fish
7,005,857 B2 2/2006 Stiene et al.
7,011,630 B2 3/2006 Desai et al.
7,018,366 B2 3/2006 Easter
7,018,568 B2 3/2006 Tierney
7,022,072 B2 4/2006 Fox et al.
7,024,236 B2 4/2006 Ford et al.
7,024,245 B2 4/2006 Lebel et al.
7,025,425 B2 4/2006 Kovatchev et al.
7,025,743 B2 4/2006 Mann et al.
7,029,444 B2 4/2006 Shin et al.
7,039,810 B1 5/2006 Nichols
7,041,068 B2 5/2006 Freeman et al.
7,041,468 B2 5/2006 Drucker et al.
7,043,287 B1 5/2006 Khalil et al.
7,049,277 B2 5/2006 Bragulla et al.
7,052,251 B2 5/2006 Nason et al.
7,052,472 B1 5/2006 Miller et al.
7,052,483 B2 5/2006 Wojcik
7,056,302 B2 6/2006 Douglas
7,074,307 B2 7/2006 Simpson et al.
7,079,977 B2 7/2006 Osorio et al.
7,081,195 B2 7/2006 Simpson et al.
7,092,891 B2 8/2006 Maus et al.
7,098,803 B2 8/2006 Mann et al.
7,108,778 B2 9/2006 Simpson et al.
7,110,803 B2 9/2006 Shults et al.
7,113,821 B1 9/2006 Sun et al.
7,133,710 B2 11/2006 Acosta et al.
7,134,999 B2 11/2006 Brauker et al.
7,136,689 B2 11/2006 Shults et al.
7,150,975 B2 12/2006 Tamada et al.
7,155,112 B2 12/2006 Uno et al.
7,163,511 B2 1/2007 Conn et al.
7,171,274 B2 1/2007 Starkweather et al.
7,183,068 B2 2/2007 Burson et al.
7,183,102 B2 2/2007 Monfre et al.
7,189,341 B2 3/2007 Li et al.
7,190,988 B2 3/2007 Say et al.
7,192,450 B2 3/2007 Brauker et al.
7,198,606 B2 4/2007 Boecker et al.
7,226,978 B2 6/2007 Tapsak et al.
7,228,163 B2 6/2007 Ackerman
7,233,817 B2 6/2007 Yen
7,261,691 B1 8/2007 Asomani
7,267,665 B2 9/2007 Steil et al.
7,276,029 B2 10/2007 Goode, Jr. et al.
7,295,867 B2 11/2007 Berner et al.
7,310,544 B2 12/2007 Brister et al.
7,317,938 B2 1/2008 Lorenz et al.
7,404,796 B2 7/2008 Ginsberg
7,474,992 B2 1/2009 Ariyur
7,591,801 B2 9/2009 Brauker et al.
7,651,845 B2 1/2010 Doyle, III et al.
7,699,964 B2 4/2010 Feldman et al.
7,766,829 B2 8/2010 Sloan et al.
7,889,069 B2 2/2011 Fifolt et al.
8,010,174 B2 8/2011 Goode et al.
8,282,549 B2 10/2012 Brauker et al.
2001/0011224 A1 8/2001 Brown
2001/0016310 A1 8/2001 Brown et al.
2001/0016682 A1 8/2001 Berner et al.
2001/0016683 A1 8/2001 Darrow et al.
2001/0020124 A1 9/2001 Tamada
2001/0029340 A1 10/2001 Mault et al.
2001/0032278 A1 10/2001 Brown et al.
2001/0037060 A1 11/2001 Thompson et al.
2001/0037069 A1 11/2001 Carlson et al.
2001/0039504 A1 11/2001 Linberg et al.
2001/0041830 A1 11/2001 Varalli et al.
2001/0044581 A1 11/2001 Mault
2001/0044588 A1 11/2001 Mault
2001/0047125 A1 11/2001 Quy
2001/0049096 A1 12/2001 Brown
2001/0049470 A1 12/2001 Mault et al.
2002/0002326 A1 1/2002 Causey, III et al.
2002/0002328 A1 1/2002 Tamada
2002/0004640 A1 1/2002 Conn et al.
2002/0010414 A1 1/2002 Coston et al.
2002/0016530 A1 2/2002 Brown
2002/0016719 A1 2/2002 Nemeth et al.
2002/0019022 A1 2/2002 Dunn et al.
2002/0019586 A1 2/2002 Teller et al.
2002/0019748 A1 2/2002 Brown
2002/0026937 A1 3/2002 Mault
2002/0027164 A1 3/2002 Mault et al.
2002/0028995 A1 3/2002 Mault
2002/0040208 A1 4/2002 Flaherty et al.
2002/0042090 A1 4/2002 Heller et al.
2002/0047867 A1 4/2002 Mault et al.
2002/0053637 A1 5/2002 Conn et al.
2002/0062069 A1 5/2002 Mault
2002/0063060 A1 5/2002 Gascoyne et al.
2002/0068858 A1 6/2002 Braig et al.
2002/0068860 A1 6/2002 Clark
2002/0072858 A1 6/2002 Cheng
2002/0077765 A1 6/2002 Mault
2002/0077766 A1 6/2002 Mault
2002/0081559 A1 6/2002 Brown et al.
2002/0083461 A1 6/2002 Hutcheson et al.
2002/0087056 A1 7/2002 Aceti et al.
2002/0091312 A1 7/2002 Berner et al.
2002/0103425 A1 8/2002 Mault
2002/0103499 A1 8/2002 Perez et al.
2002/0106709 A1 8/2002 Potts et al.
2002/0107433 A1 8/2002 Mault
2002/0107476 A1 8/2002 Mann et al.
2002/0109600 A1 8/2002 Mault et al.
2002/0119711 A1 8/2002 Van Antwerp et al.
2002/0124017 A1 9/2002 Mault
2002/0128594 A1 9/2002 Das et al.
2002/0130042 A1 9/2002 Moerman et al.
2002/0133378 A1 9/2002 Mault et al.
2002/0147135 A1 10/2002 Schnell
2002/0161286 A1 10/2002 Gerber et al.
2002/0161288 A1 10/2002 Shin et al.
2002/0169635 A1 * 11/2002 Shillingburg .................... 705/2
2002/0177764 A1 11/2002 Sohrab
2003/0023182 A1 1/2003 Mault et al.

(56) References Cited

U.S. PATENT DOCUMENTS

| | | | | |
|---|---|---|---|---|
| 2003/0023317 | A1 | 1/2003 | Brauker et al. | |
| 2003/0028089 | A1 | 2/2003 | Galley et al. | |
| 2003/0028120 | A1 | 2/2003 | Mault et al. | |
| 2003/0032077 | A1 | 2/2003 | Itoh et al. | |
| 2003/0032867 | A1 | 2/2003 | Crothall et al. | |
| 2003/0032868 | A1 | 2/2003 | Graskov et al. | |
| 2003/0032874 | A1 | 2/2003 | Rhodes et al. | |
| 2003/0040683 | A1 | 2/2003 | Rule et al. | |
| 2003/0042137 | A1 | 3/2003 | Mao et al. | |
| 2003/0050537 | A1 | 3/2003 | Wessel | |
| 2003/0050546 | A1 | 3/2003 | Desai et al. | |
| 2003/0065257 | A1 | 4/2003 | Mault et al. | |
| 2003/0065273 | A1 | 4/2003 | Mault et al. | |
| 2003/0065274 | A1 | 4/2003 | Mault et al. | |
| 2003/0065275 | A1 | 4/2003 | Mault et al. | |
| 2003/0065308 | A1 | 4/2003 | Lebel et al. | |
| 2003/0100040 | A1 | 5/2003 | Bonnecaze et al. | |
| 2003/0100821 | A1 | 5/2003 | Heller et al. | |
| 2003/0105407 | A1 | 6/2003 | Pearce et al. | |
| 2003/0108976 | A1 | 6/2003 | Braig et al. | |
| 2003/0122021 | A1 | 7/2003 | McConnell et al. | |
| 2003/0130616 | A1 | 7/2003 | Steil et al. | |
| 2003/0134347 | A1 | 7/2003 | Heller et al. | |
| 2003/0135100 | A1 | 7/2003 | Kim et al. | |
| 2003/0135333 | A1 | 7/2003 | Aceti et al. | |
| 2003/0153820 | A1 | 8/2003 | Berner et al. | |
| 2003/0153821 | A1 | 8/2003 | Berner et al. | |
| 2003/0158472 | A1 | 8/2003 | Sohrab | |
| 2003/0158707 | A1 | 8/2003 | Doi | |
| 2003/0168338 | A1 | 9/2003 | Gao et al. | |
| 2003/0175806 | A1 | 9/2003 | Rule et al. | |
| 2003/0176183 | A1 | 9/2003 | Drucker et al. | |
| 2003/0176933 | A1 | 9/2003 | Lebel et al. | |
| 2003/0181851 | A1 | 9/2003 | Mann et al. | |
| 2003/0181852 | A1 | 9/2003 | Mann et al. | |
| 2003/0187338 | A1 | 10/2003 | Say et al. | |
| 2003/0187525 | A1 | 10/2003 | Mann et al. | |
| 2003/0191376 | A1 | 10/2003 | Samuels et al. | |
| 2003/0191377 | A1 | 10/2003 | Robinson et al. | |
| 2003/0191431 | A1 | 10/2003 | Mann et al. | |
| 2003/0195403 | A1 | 10/2003 | Berner et al. | |
| 2003/0195462 | A1 | 10/2003 | Mann et al. | |
| 2003/0199790 | A1 | 10/2003 | Boecker et al. | |
| 2003/0199791 | A1 | 10/2003 | Boecker et al. | |
| 2003/0199903 | A1 | 10/2003 | Boecker et al. | |
| 2003/0208110 | A1 | 11/2003 | Mault et al. | |
| 2003/0208113 | A1 | 11/2003 | Mault et al. | |
| 2003/0208133 | A1 | 11/2003 | Mault | |
| 2003/0208409 | A1 | 11/2003 | Mault | |
| 2003/0212364 | A1 | 11/2003 | Mann et al. | |
| 2003/0212379 | A1 | 11/2003 | Bylund et al. | |
| 2003/0217966 | A1 | 11/2003 | Tapsak et al. | |
| 2003/0226695 | A1 | 12/2003 | Mault | |
| 2003/0229514 | A2 | 12/2003 | Brown | |
| 2003/0232370 | A1 | 12/2003 | Trifiro | |
| 2003/0235817 | A1 | 12/2003 | Bartkowiak et al. | |
| 2004/0010186 | A1 | 1/2004 | Kimball et al. | |
| 2004/0010207 | A1 | 1/2004 | Flaherty et al. | |
| 2004/0011671 | A1 | 1/2004 | Shults et al. | |
| 2004/0018486 | A1 | 1/2004 | Dunn et al. | |
| 2004/0024553 | A1 | 2/2004 | Monfre et al. | |
| 2004/0039256 | A1 | 2/2004 | Kawatahara et al. | |
| 2004/0040840 | A1 | 3/2004 | Mao et al. | |
| 2004/0045879 | A1 | 3/2004 | Shults et al. | |
| 2004/0054263 | A1 | 3/2004 | Moerman et al. | |
| 2004/0059201 | A1 | 3/2004 | Ginsberg | |
| 2004/0064068 | A1 | 4/2004 | DeNuzzio et al. | |
| 2004/0069164 | A1 | 4/2004 | Nakamura et al. | |
| 2004/0072357 | A1 | 4/2004 | Stiene et al. | |
| 2004/0073095 | A1 | 4/2004 | Causey, III et al. | |
| 2004/0096959 | A1 | 5/2004 | Stiene et al. | |
| 2004/0106858 | A1 | 6/2004 | Say et al. | |
| 2004/0108226 | A1 | 6/2004 | Polychronakos et al. | |
| 2004/0122353 | A1 | 6/2004 | Shahmirian et al. | |
| 2004/0122489 | A1 | 6/2004 | Mazar et al. | |
| 2004/0122530 | A1 | 6/2004 | Hansen et al. | |
| 2004/0133164 | A1 | 7/2004 | Funderburk et al. | |
| 2004/0138588 | A1 | 7/2004 | Saikley et al. | |
| 2004/0152622 | A1 | 8/2004 | Keith et al. | |
| 2004/0153585 | A1 | 8/2004 | Kawatahara et al. | |
| 2004/0162473 | A1 | 8/2004 | Sohrab | |
| 2004/0164961 | A1 | 8/2004 | Bal et al. | |
| 2004/0167383 | A1 | 8/2004 | Kim et al. | |
| 2004/0167464 | A1 | 8/2004 | Ireland et al. | |
| 2004/0167801 | A1 | 8/2004 | Say et al. | |
| 2004/0171921 | A1 | 9/2004 | Say et al. | |
| 2004/0172284 | A1 | 9/2004 | Sullivan et al. | |
| 2004/0176672 | A1 | 9/2004 | Silver et al. | |
| 2004/0176913 | A1 | 9/2004 | Kawatahara et al. | |
| 2004/0186362 | A1 | 9/2004 | Brauker et al. | |
| 2004/0186365 | A1 | 9/2004 | Jin et al. | |
| 2004/0193025 | A1 | 9/2004 | Steil et al. | |
| 2004/0193090 | A1 | 9/2004 | Lebel et al. | |
| 2004/0199059 | A1 | 10/2004 | Brauker et al. | |
| 2004/0202576 | A1 | 10/2004 | Aceti et al. | |
| 2004/0204687 | A1 | 10/2004 | Mogensen et al. | |
| 2004/0208780 | A1 | 10/2004 | Faries et al. | |
| 2004/0225338 | A1 | 11/2004 | Lebel et al. | |
| 2004/0248204 | A1 | 12/2004 | Moerman | |
| 2004/0249250 | A1 | 12/2004 | McGee et al. | |
| 2004/0249253 | A1 | 12/2004 | Racchini et al. | |
| 2004/0249254 | A1 | 12/2004 | Racchini et al. | |
| 2004/0249999 | A1 | 12/2004 | Connolly et al. | |
| 2004/0253736 | A1 | 12/2004 | Stout et al. | |
| 2004/0254429 | A1 | 12/2004 | Yang | |
| 2004/0254433 | A1 | 12/2004 | Bandis et al. | |
| 2004/0254434 | A1 | 12/2004 | Goodnow et al. | |
| 2004/0260363 | A1 | 12/2004 | Arx et al. | |
| 2004/0260478 | A1 * | 12/2004 | Schwamm | 702/20 |
| 2004/0263354 | A1 | 12/2004 | Mann et al. | |
| 2004/0267300 | A1 | 12/2004 | Mace | |
| 2005/0003470 | A1 | 1/2005 | Nelson et al. | |
| 2005/0004494 | A1 | 1/2005 | Perez et al. | |
| 2005/0010087 | A1 | 1/2005 | Banet et al. | |
| 2005/0010269 | A1 | 1/2005 | Lebel et al. | |
| 2005/0016276 | A1 | 1/2005 | Guan et al. | |
| 2005/0027177 | A1 | 2/2005 | Shin et al. | |
| 2005/0027179 | A1 | 2/2005 | Berner et al. | |
| 2005/0027180 | A1 | 2/2005 | Goode, Jr. et al. | |
| 2005/0027181 | A1 | 2/2005 | Goode, Jr. et al. | |
| 2005/0027462 | A1 | 2/2005 | Goode, Jr. et al. | |
| 2005/0027463 | A1 | 2/2005 | Goode, Jr. et al. | |
| 2005/0031689 | A1 | 2/2005 | Shults et al. | |
| 2005/0033132 | A1 | 2/2005 | Shults et al. | |
| 2005/0038674 | A1 | 2/2005 | Braig et al. | |
| 2005/0038680 | A1 | 2/2005 | McMahon | |
| 2005/0043598 | A1 | 2/2005 | Goode, Jr. et al. | |
| 2005/0043894 | A1 | 2/2005 | Fernandez | |
| 2005/0049179 | A1 * | 3/2005 | Davidson et al. | 514/3 |
| 2005/0049473 | A1 | 3/2005 | Desai et al. | |
| 2005/0054909 | A1 | 3/2005 | Petisce et al. | |
| 2005/0055474 | A1 | 3/2005 | Yang | |
| 2005/0065464 | A1 | 3/2005 | Talbot et al. | |
| 2005/0090607 | A1 | 4/2005 | Tapsak et al. | |
| 2005/0096516 | A1 | 5/2005 | Soykan et al. | |
| 2005/0112169 | A1 | 5/2005 | Brauker et al. | |
| 2005/0113653 | A1 | 5/2005 | Fox et al. | |
| 2005/0113657 | A1 | 5/2005 | Alarcon et al. | |
| 2005/0113658 | A1 | 5/2005 | Jacobson et al. | |
| 2005/0114068 | A1 | 5/2005 | Chey et al. | |
| 2005/0118726 | A1 | 6/2005 | Schultz et al. | |
| 2005/0121322 | A1 | 6/2005 | Say et al. | |
| 2005/0124873 | A1 | 6/2005 | Shults et al. | |
| 2005/0131346 | A1 | 6/2005 | Douglas | |
| 2005/0137471 | A1 | 6/2005 | Haar et al. | |
| 2005/0137530 | A1 | 6/2005 | Campbell et al. | |
| 2005/0143635 | A1 | 6/2005 | Kamath et al. | |
| 2005/0143636 | A1 | 6/2005 | Zhang et al. | |
| 2005/0148003 | A1 | 7/2005 | Kieth et al. | |
| 2005/0154271 | A1 | 7/2005 | Rasdal et al. | |
| 2005/0161346 | A1 | 7/2005 | Simpson et al. | |
| 2005/0171503 | A1 | 8/2005 | Van Den Berghe et al. | |
| 2005/0171513 | A1 | 8/2005 | Mann et al. | |
| 2005/0173245 | A1 | 8/2005 | Feldman et al. | |

(56) References Cited

U.S. PATENT DOCUMENTS

2005/0176136 A1 8/2005 Burd et al.
2005/0177036 A1 8/2005 Shults et al.
2005/0181012 A1 8/2005 Saint et al.
2005/0182306 A1 8/2005 Sloan
2005/0182451 A1 8/2005 Griffin et al.
2005/0187720 A1 8/2005 Goode, Jr. et al.
2005/0192557 A1 9/2005 Brauker et al.
2005/0195930 A1 9/2005 Spital et al.
2005/0199494 A1 9/2005 Say et al.
2005/0203360 A1 9/2005 Brauker et al.
2005/0203707 A1 9/2005 Tsutsui et al.
2005/0214892 A1 9/2005 Kovatchev et al.
2005/0215871 A1 9/2005 Feldman et al.
2005/0215872 A1 9/2005 Berner et al.
2005/0221504 A1 10/2005 Petruno et al.
2005/0239154 A1 10/2005 Feldman et al.
2005/0239156 A1 10/2005 Drucker et al.
2005/0245795 A1 11/2005 Goode, Jr. et al.
2005/0245799 A1 11/2005 Brauker et al.
2005/0251083 A1 11/2005 Carr-Brendel et al.
2005/0261660 A1 11/2005 Choi
2005/0267780 A1 12/2005 Ray et al.
2005/0271546 A1 12/2005 Gerber et al.
2005/0271547 A1 12/2005 Gerber et al.
2005/0272640 A1 12/2005 Doyle, III et al.
2005/0272985 A1 12/2005 Kotulla et al.
2005/0277164 A1 12/2005 Drucker et al.
2005/0277912 A1* 12/2005 John .......................... 604/890.1
2005/0287620 A1 12/2005 Heller et al.
2006/0001538 A1 1/2006 Kraft et al.
2006/0001550 A1 1/2006 Mann et al.
2006/0001551 A1 1/2006 Kraft et al.
2006/0003398 A1 1/2006 Heller et al.
2006/0004271 A1 1/2006 Peyser et al.
2006/0007017 A1 1/2006 Mann et al.
2006/0015020 A1 1/2006 Neale et al.
2006/0015024 A1 1/2006 Brister et al.
2006/0016700 A1 1/2006 Brister et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0025663 A1 2/2006 Talbot et al.
2006/0031094 A1 2/2006 Cohen et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0036187 A1 2/2006 Vos et al.
2006/0040402 A1 2/2006 Brauker et al.
2006/0052679 A1 3/2006 Kotulla et al.
2006/0058602 A1 3/2006 Kwiatkowski et al.
2006/0063218 A1 3/2006 Bartkowiak et al.
2006/0074564 A1 4/2006 Bartkowiak et al.
2006/0173406 A1 8/2006 Hayes et al.
2006/0173444 A1 8/2006 Choy et al.
2006/0189863 A1 8/2006 Peyser et al.
2006/0195029 A1 8/2006 Shults et al.
2006/0222566 A1 10/2006 Brauker et al.
2006/0226985 A1 10/2006 Goodnow et al.
2006/0247508 A1 11/2006 Fennell
2006/0247985 A1 11/2006 Liamos et al.
2006/0253296 A1 11/2006 Liisberg et al.
2006/0272652 A1 12/2006 Stocker et al.
2006/0277443 A1 12/2006 You et al.
2007/0027381 A1 2/2007 Stafford
2007/0032706 A1 2/2007 Kamath et al.
2007/0033074 A1 2/2007 Nitzan et al.
2007/0060803 A1 3/2007 Liljeryd et al.
2007/0060814 A1 3/2007 Stafford
2007/0060869 A1 3/2007 Tolle et al.
2007/0073129 A1 3/2007 Shah et al.
2007/0078314 A1 4/2007 Grounsell et al.
2007/0078320 A1 4/2007 Stafford
2007/0078321 A1 4/2007 Mazza et al.
2007/0078322 A1 4/2007 Stafford
2007/0078323 A1 4/2007 Reggiardo et al.
2007/0093786 A1 4/2007 Goldsmith et al.
2007/0106135 A1 5/2007 Sloan et al.
2007/0149873 A1 6/2007 Say et al.
2007/0149874 A1 6/2007 Say et al.
2007/0151869 A1 7/2007 Heller et al.
2007/0161879 A1 7/2007 Say et al.
2007/0161880 A1 7/2007 Say et al.
2007/0163880 A1 7/2007 Woo et al.
2007/0173706 A1 7/2007 Neinast et al.
2007/0173761 A1 7/2007 Kanderian, Jr. et al.
2007/0179370 A1 8/2007 Say et al.
2007/0179372 A1 8/2007 Say et al.
2007/0191699 A1 8/2007 Say et al.
2007/0191700 A1 8/2007 Say et al.
2007/0191702 A1 8/2007 Yodfat et al.
2007/0203407 A1 8/2007 Hoss et al.
2007/0203408 A1 8/2007 Say et al.
2007/0203410 A1 8/2007 Say et al.
2007/0203411 A1 8/2007 Say et al.
2007/0203966 A1 8/2007 Brauker et al.
2007/0208247 A1 9/2007 Say et al.
2007/0213610 A1 9/2007 Say et al.
2007/0213657 A1 9/2007 Jennewine et al.
2007/0215491 A1 9/2007 Heller et al.
2007/0218097 A1 9/2007 Heller et al.
2007/0235331 A1 10/2007 Simpson et al.
2007/0244380 A1 10/2007 Say et al.
2007/0249919 A1 10/2007 Say et al.
2007/0249920 A1 10/2007 Say et al.
2007/0249922 A1 10/2007 Peyser et al.
2007/0271285 A1 11/2007 Eichorn et al.
2007/0282299 A1 12/2007 Hellwig
2008/0004515 A1 1/2008 Jennewine et al.
2008/0004601 A1 1/2008 Jennewine et al.
2008/0009692 A1 1/2008 Stafford
2008/0021666 A1 1/2008 Goode, Jr. et al.
2008/0033254 A1 2/2008 Kamath et al.
2008/0039702 A1 2/2008 Hayter et al.
2008/0045824 A1 2/2008 Tapsak et al.
2008/0052317 A1* 2/2008 Francis et al. ............. 707/104.1
2008/0067627 A1 3/2008 Boeck et al.
2008/0071156 A1 3/2008 Brister et al.
2008/0083617 A1 4/2008 Brister et al.
2008/0086042 A1 4/2008 Brister et al.
2008/0086044 A1 4/2008 Brister et al.
2008/0086273 A1 4/2008 Shults et al.
2008/0108942 A1 5/2008 Brister et al.
2008/0119708 A1 5/2008 Budiman
2008/0154513 A1 6/2008 Kovatchev et al.
2008/0161666 A1 7/2008 Feldman et al.
2008/0163001 A1 7/2008 Ko et al.
2008/0172205 A1 7/2008 Breton et al.
2008/0267823 A1 10/2008 Wang et al.
2008/0300572 A1 12/2008 Rankers et al.
2008/0319085 A1* 12/2008 Wright et al. ................. 514/646
2008/0319279 A1 12/2008 Ramsay et al.
2008/0319296 A1 12/2008 Bernstein et al.
2009/0006061 A1 1/2009 Thukral et al.
2009/0006133 A1 1/2009 Weinert et al.
2009/0054745 A1 2/2009 Jennewine et al.
2009/0054748 A1 2/2009 Feldman et al.
2009/0068954 A1 3/2009 Reggiardo et al.
2009/0105560 A1 4/2009 Solomon
2009/0105570 A1 4/2009 Sloan et al.
2009/0253973 A1 10/2009 Bashan et al.
2010/0011130 A1 1/2010 Tasher et al.
2010/0025238 A1 2/2010 Gottlieb et al.
2010/0105999 A1 4/2010 Dixon et al.
2010/0119881 A1 5/2010 Patel et al.
2010/0152554 A1 6/2010 Steine et al.

(56) References Cited

U.S. PATENT DOCUMENTS

| | | | |
|---|---|---|---|
| 2010/0168546 | A1 | 7/2010 | Kamath et al. |
| 2010/0198142 | A1 | 8/2010 | Sloan et al. |
| 2010/0312176 | A1 | 12/2010 | Lauer et al. |
| 2010/0324403 | A1 | 12/2010 | Brister et al. |

FOREIGN PATENT DOCUMENTS

| | | |
|---|---|---|
| CA | 2498682 | 9/2005 |
| CA | 2555749 | 9/2005 |
| CA | 2632709 | 6/2007 |
| CA | 2615575 | 6/2008 |
| CA | 2701374 | 4/2009 |
| DE | 4234553 | 1/1995 |
| DE | 4401400 | 7/1995 |
| EP | 0010375 | 4/1980 |
| EP | 1579690 | 11/1980 |
| EP | 0026995 | 4/1981 |
| EP | 0048090 | 3/1982 |
| EP | 0078636 | 5/1983 |
| EP | 0080304 | 6/1983 |
| EP | 0096228 | 12/1983 |
| EP | 0096288 | 12/1983 |
| EP | 0098592 | 1/1984 |
| EP | 0125139 | 11/1984 |
| EP | 0127958 | 12/1984 |
| EP | 0136362 | 4/1985 |
| EP | 0170375 | 2/1986 |
| EP | 0177743 | 4/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0320109 | 6/1989 |
| EP | 0353328 | 2/1990 |
| EP | 0359831 | 3/1990 |
| EP | 0368209 | 5/1990 |
| EP | 0368290 | 5/1990 |
| EP | 0390390 | 10/1990 |
| EP | 0396788 | 11/1990 |
| EP | 0400918 | 12/1990 |
| EP | 0453283 | 10/1991 |
| EP | 0470290 | 2/1992 |
| EP | 0504835 | 9/1992 |
| EP | 0286118 | 1/1995 |
| EP | 0653718 | 5/1995 |
| EP | 0800082 | 10/1997 |
| EP | 0880936 | 12/1998 |
| EP | 0970655 | 1/2000 |
| EP | 1034734 | 9/2000 |
| EP | 1048264 | 11/2000 |
| EP | 1445746 | 8/2004 |
| EP | 1956371 | 8/2008 |
| EP | 2260757 | 12/2010 |
| GB | 1394171 | 5/1975 |
| GB | 1579690 | 11/1980 |
| GB | 1599241 | 9/1981 |
| GB | 2073891 | 10/1981 |
| GB | 2154003 | 8/1985 |
| GB | 2194892 | 3/1988 |
| GB | 2204408 | 11/1988 |
| GB | 2225637 | 6/1990 |
| GB | 2254436 | 10/1992 |
| JP | 8-154903 | 6/1996 |
| JP | 2004-000555 | 8/2004 |
| WO | WO-85/05119 | 11/1985 |
| WO | WO-86/00513 | 1/1986 |
| WO | WO-87/00513 | 1/1987 |
| WO | WO-87/06040 | 10/1987 |
| WO | WO-89/02246 | 3/1989 |
| WO | WO-89/05119 | 6/1989 |
| WO | WO-89/08713 | 9/1989 |
| WO | WO-90/00367 | 1/1990 |
| WO | WO-90/05300 | 5/1990 |
| WO | WO-90/05910 | 5/1990 |
| WO | WO-91/01680 | 2/1991 |
| WO | WO-91/04704 | 4/1991 |
| WO | WO-91/15993 | 10/1991 |
| WO | WO-92/13271 | 8/1992 |
| WO | WO-94/20602 | 9/1994 |
| WO | WO-94/27140 | 11/1994 |
| WO | WO-95/06240 | 3/1995 |
| WO | WO-96/07908 | 3/1996 |
| WO | WO-96/25089 | 8/1996 |
| WO | WO-96/30431 | 10/1996 |
| WO | WO-96/35370 | 11/1996 |
| WO | WO-97/02847 | 1/1997 |
| WO | WO-97/19344 | 5/1997 |
| WO | WO-97/20207 | 6/1997 |
| WO | WO-97/41421 | 11/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-97/46868 | 12/1997 |
| WO | WO-98/09167 | 3/1998 |
| WO | WO-98/24366 | 6/1998 |
| WO | WO-98/35053 | 8/1998 |
| WO | WO-98/52045 | 11/1998 |
| WO | WO-98/52293 | 11/1998 |
| WO | WO-99/05966 | 2/1999 |
| WO | WO-99/32883 | 7/1999 |
| WO | WO-99/56613 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/33065 | 6/2000 |
| WO | WO-00/49940 | 8/2000 |
| WO | WO-00/59370 | 10/2000 |
| WO | WO-00/62664 | 10/2000 |
| WO | WO-00/62665 | 10/2000 |
| WO | WO-00/78210 | 12/2000 |
| WO | WO-00/78992 | 12/2000 |
| WO | WO-01/24038 | 4/2001 |
| WO | WO-01/33216 | 5/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/67009 | 9/2001 |
| WO | WO-02/13686 | 2/2002 |
| WO | WO-02/16905 | 2/2002 |
| WO | WO-02/17210 | 2/2002 |
| WO | WO-02/058537 | 8/2002 |
| WO | WO-02/078512 | 10/2002 |
| WO | WO-03/036583 | 5/2003 |
| WO | WO-03/076893 | 9/2003 |
| WO | WO-03/082091 | 10/2003 |
| WO | WO-2004/015539 | 2/2004 |
| WO | WO-2004/061420 | 7/2004 |
| WO | WO-2004/084820 | 10/2004 |
| WO | WO-2005/089103 | 9/2005 |
| WO | WO-2006/037109 | 4/2006 |
| WO | WO-2006/118947 | 11/2006 |
| WO | WO-2006/119084 | 11/2006 |
| WO | WO-2007/016399 | 2/2007 |
| WO | WO-2007/027381 | 3/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/053832 | 5/2007 |
| WO | WO-2007/056638 | 5/2007 |
| WO | WO-2007/065285 | 6/2007 |
| WO | WO-2007/101260 | 9/2007 |
| WO | WO-2007/120363 | 10/2007 |
| WO | WO-2007/143225 | 12/2007 |

(56) References Cited

FOREIGN PATENT DOCUMENTS

WO WO-2007/149319 12/2007
WO WO 2008/001366 1/2008
WO WO-2008/003003 1/2008
WO WO-2008/005780 1/2008
WO WO-2011/1046 I6 9/2011

OTHER PUBLICATIONS

International Search Report and Written Opinion of the International Searching Authority for PCT Application No. PCT/US2008/054187 filed Feb. 16, 2008 to Abbott Diabetes Care, Inc. mailed Aug. 15, 2008.
International Preliminary Report on Patentability and Written Opinion of the International Searching Authority for PCT Application No. PCT/US2008/054187 filed Feb. 16, 2008, mailed Aug. 27, 2009.
Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1070.
Bremer, T. M., et al., "Benchmark Data from the Literature for Evaluation of New Glucose Sensing Technologies", *Diabetes Technology & Therapeutics*, vol. 3, No. 3, 2001, pp. 409-418.
Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.
Garg, S., et al., "Improvement in Glycemic Excursions with a Transcutaneous, Real-Time Continuous Glucose Sensor", *Diabetes Care*, vol. 29, No. 1, 2006, pp. 44-50.
Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.
Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.
Mougiakakou, et al., "A Real Time Simulation Model of Glucose-Insulin Metabolism for Type 1 Diabetes Patients", *Proceedings of the 2005 IEEE*, 2005, pp. 298-301.
Panteleon, A. E., et al., "The Role of the Independent Variable to Glucose Sensor Calibration", *Diabetes Technology & Therapeutics*, vol. 5, No. 3, 2003, pp. 401-410.
Parker, R., et al., "Robust H∞ Glucose Control in Diabetes Using a Physiological Model", *AIChE Journal*, vol. 46, No. 12, 2000, pp. 2537-2549.
Japanese Patent Application No. 2009-550163, Original Language and Translation of Office Action mailed Aug. 21, 2012.
Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.
Abstract of Japanese Publication No. JP-55-010581, Published Jan. 5, 1980.
Abstract of Japanese Publication No. JP-55-010583, Published Jan. 5, 1980.
Abstract of Japanese Publication No. JP-55-010584, Published Jan. 5, 1980.
Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.
Albery, W. J., et al., "Amperometric Enzyme Electrodes", *Philosophical Transactions of the Royal Society of London*, vol. 316, 1987, pp. 107-119.
Alcock, S. J., et al., "Continuous Analyte Monitoring to Aid Clinical Practice", *IEEE Engineering in Medicine and Biology Magazine*, 1994, pp. 319-325.
Anderson, L. B., et al., "Thin-Layer Electrochemistry: Steady-State Methods of Studying Rate Processes", *Journal of ElectroAnalytical Chemistry*, vol. 10, 1965, pp. 295-305.
Armour, J. C., et al., "Application of Chronic Intravascular Blood Glucose Sensor in Dogs", Diabetes, vol. 39, 1990, pp. 1519-1526.
Bartlett, P. N., et al., "Covalent Binding of Electron Relays to Glucose Oxidase", *Journal of the Chemical Society, Chemical Communications*, 1987, pp. 1603-1604.
Bartlett, P. N., et al., "Modification of Glucose Oxidase by Tetrathiafulvalene" *Journal of the Chemical Society, Chemical Communications*, 1990, pp. 1135-1136.
Bartlett, P. N., et al., "Strategies for the Development of Amperometric Enzyme Electrodes", *Biosensors*, vol. 3, 1987/88, pp. 359-379.
Bennion, N., et al., "Alternate Site Glucose Testing: A Crossover Design", *Diabetes Technology & Therapeutics*, vol. 4, No. 1, 2002, pp. 25-33.
Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.
Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.
Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.
Boedeker Plastics, Inc., "Polyethylene Specifications", *Web Page of Boedeker.com*, 2007, pp. 1-3.
Brandt, J., et al., "Covalent Attachment of Proteins to Polysaccharide Carriers by Means of Benzoquinone", *Biochimica et Biophysica Acta*, vol. 386, 1975, pp. 196-202.
Brooks, S. L., et al., "Development of an On-Line Glucose Sensor for Fermentation Monitoring", *Biosensors*, vol. 3, 1987/88, pp. 45-56.
Brownlee, M., et al., "A Glucose-Controlled Insulin-Delivery System: Semisynthetic Insulin Bound to Lectin", *Science*, vol. 206, 1979, 1190-1191.
Cass, A. E., et al., "Ferricinum Ion As an Electron Acceptor for Oxido-Reductases", *Journal of ElectroAnalytical Chemistry*, vol. 190, 1985, pp. 117-127.
Cass, A. E., et al., "Ferrocene-Medicated Enzyme Electrode for Amperometric Determination of Glucose", *Analytical Chemistry*, vol. 56, No. 4, 1984, 667-671.
Castner, J. F., et al., "Mass Transport and Reaction Kinetic Parameters Determined Electrochemically for Immobilized Glucose Oxidase", *Biochemistry*, vol. 23 No. 10, 1984, 2203-2210.
Claremont, D. J., et al., "Biosensors for Continuous In Vivo Glucose Monitoring", *Proceedings of the Annual International Conference of the IEEE Engineering in Medicine and Biology Society*, vol. 10, 1988.
Clark Jr., L. C., et al., "Differential Anodic Enzyme Polarography for the Measurement of Glucose", *Oxygen Transport to Tissue: Instrumentation, Methods, and Physiology*, 1973, pp. 127-133.
Clark Jr., L. C., et al., "Electrode Systems for Continuous Monitoring in Cardiovascular Surgery", *Annals New York Academy of Sciences*, 1962, pp. 29-45.
Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.
Clarke, W. L., et al., "Evaluating Clinical Accuracy of Systems for Self-Monitoring of Blood Glucose", *Diabetes Care*, vol. 10, No. 5, 1987, pp. 622-628.
Complaint, "*Abbott Diabetes Care, Inc.* v. *Dexcom, Inc.*", filed Aug. 11, 2005.
Complaint, Amended, "*Abbott Diabetes Care, Inc.* v. *Dexcom, Inc.*", filed Jun. 27, 2006.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

(56) References Cited

OTHER PUBLICATIONS

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.
Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.
Davis, G., "Electrochemical Techniques for the Development of Amperometric Biosensors", *Biosensors*, vol. 1, 1985, pp. 161-178.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.
Degani, Y., et al., "Electrical Communication Between Redox Centers of Glucose Oxidase and Electrodes via Electrostatically and Covalently Bound Redox Polymers",*Journal of the American Chemical Society*, vol. 111, 1989, pp. 2357-2358.
Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.
Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.
Ellis, C. D., et al., "Selectivity and Directed Charge Transfer through an Electroactive Metallopolymer Film", *Journal of the American Chemical Society*, vol. 103, No. 25, 1981, pp. 7480-7483.
Engstrom, R. C., "Electrochemical Pretreatment of Glassy Carbon Electrodes", *Analytical Chemistry*, vol. 54, No. 13, 1982, pp. 2310-2314.
Engstrom, R. C., et al., "Characterization of Electrochemically Pretreated Glassy Carbon Electrodes", *Analytical Chemistry*, vol. 56, No. 2, 1984, pp. 136-141.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Continuous Glucose Change", *Abbott Diabetes Care, Inc. Freestyle Navigator Monitor Glucose Pamphlet*.
Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.
Fischer, H., et al., "Intramolecular Electron Transfer Medicated by 4,4'-Bypyridine and Related Bridging Groups", *Journal of the American Chemical Society*, vol. 98. No. 18, 1976, pp. 5512-5517.
Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.
Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.
Foulds, N. C., et al., "Immobilization of Glucose Oxidase in Ferrocene-Modified Pyrrole Polymers", *Analytical Chemistry*, vol. 60, No. 22, 1988, pp. 2473-2478.
Frew, J. E., et al., "Electron-Transfer Biosensors", *Philosophical Transactions of the Royal Society of London*, vol. 316, 1987, pp. 95-106.
Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.
Gorton, L., et al., "Selective Detection in Flow Analysis Based on the Combination of Immobilized Enzymes and Chemically Modified Electrodes", *Analytica Chimica Acta*, vol. 250, 1991, pp. 203-248.
Graham, N. B., "Poly(ethylene oxide) and Related Hydrogels," *Hydrogels in Medicine and Pharmacy, vol. II: Polymers*, Chapter 4, 1987, pp. 95-113.
Gregg, B. A., et al., "Cross-Linked Redox Gels Containing Glucose Oxidase for Amperometric Bionsensor Applications", *Analytical Chemistry*, vol. 62, No. 3, 1990, pp. 258-263.
Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.
Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.
Hamilton, "Hamilton Needle Gauge Index", www.hamiltoncompany.com.
Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.
Hawkridge, F. M., et al., "Indirect Coulometric Titration of Biological Electron Transport Components", *Analytical Chemistry*, vol. 45, No. 7, 1973, pp. 1021-1027.
Heller, A., "Electrical Connection Enzyme Redox Centers to Electrodes", *Journal of Physical Chemistry*, vol. 96, No. 9, 1990, pp. 3579-3587.
Heller, A., "Electrical Wiring of Redox Enzymes", *Accounts of Chemical Research vol. 23*, No. 5, 1990, 128-134.
Heller, A., et al., "Amperometric Biosensors Based on Three-Dimensional Hydrogel-Forming Epoxy Networks", *Sensors and Actuators B*, vol. 13-14, 1993, pp. 180-183.
Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.
Ianniello, R. M., et al., "Immobilized Enzyme Chemically Modified Electrode as an Amperometric Sensor", *Analytical Chemistry*, vol. 53, No. 13, 1981, pp. 2090-2095.
Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.
Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, J. M., et al., "Potential-Dependent Enzymatic Activity in an Enzyme Thin-Layer Cell", *Analytical Chemistry*, vol. 54, No. 8, 1982, pp. 1377-1383.
Johnson, K. W., "Reproducible Electrodeposition of Biomolecules for the Fabrication of Miniature Elcctroenzymatic Biosensors", *Sensors and Actuators B*, vol. 5, 1991, pp. 85-89.
Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.
Johnson, P. C., "Peripheral Circulation", *John Wiley & Sons*, 1978, pp. 198.

(56) References Cited

OTHER PUBLICATIONS

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.
Josowicz, M., et al., "Electrochemical Pretreatment of Thin Film Platinum Electrodes", *Journal of the Electrochemical Society*, vol. 135 No. 1, 1988, pp. 112-115.
Jungheim, K., et al., "How Rapid Does Glucose Concentration Change in Daily Life of Patients with Type 1 Diabetes?", pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.
Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.
Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.
Kenausis, G., et al., "'Wiring' of Glucose Oxidase and Lactate Oxidase Within a Hydrogel Made with Poly(vinyl pyridine) complexed with $[Os(4,4'\text{-dimethoxy-}2,2'\text{-bipyridine})_2Cl]^{+/2+}$", *Journal of the Chemical Society, Faraday Transactions*, vol. 92, No. 20, 1996, pp. 4131-4136.
Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.
Korf, J., et al., "Monitoring of Glucose and Lactate Using Microdialysis: Applications in Neonates and Rat Brain," *Developmental Neuroscience*, vol. 15, 1993, pp. 240-246.
Koudelka, M., et al., "In-Vivo Behaviour of Hypodermically Implanted Microfabricated Glucose Sensors", *Biosensors & Bioelectronics*, vol. 6, 1991, pp. 31-36.
Kulys, J., et al., "Mediatorless Peroxidase Electrode and Preparation of Bienzyme Sensors", *Bioelectrochemistry and Bioenergetics*, vol. 24, 1990, pp. 305-311.
Lager, W., et al., "Implantable Electrocatalytic Glucose Sensor", *Hormone Metabolic Research*, vol. 26, 1994, pp. 526-530.
Laurell, T., "A Continuous Glucose Monitoring System Based on Microdialysis", *Journal of Medical Engineering & Technology*, vol. 16, No. 5, 1992, pp. 187-193.
Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Maidan, R., et al., "Elimination of Electrooxidizable Interferant-Produced Currents in Amperometric Biosensors", *Analytical Chemistry*, vol. 64, No. 23, 1992, pp. 2889-2896.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
Marko-Varga, G., et al., "Enzyme-Based Biosensor as a Selective Detection Unit in Column Liquid Chromatography", *Journal of Chromatography A*, vol. 660, 1994, pp. 153-167.
Mastrototaro, J. J., et al., "An Electroenzymatic Glucose Sensor Fabricated on a Flexible Substrate", *Sensors and Actuators B*, vol. 5, 1991, pp. 139-144.
Mauras, N., et al., "Lack of Accuracy of Continuous Glucose Sensors in Healthy, Nondiabetic Children: Results of the Diabetes Research in Children Network (DirecNet) Accuracy Study," Journal of Pediatrics, 2004, pp. 770-775.
McGarraugh, G., et al., "Glucose Measurements Using Blood Extracted from the Forearm and the Finger", *TheraSense, Inc.*, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.
Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.
Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.
Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.
Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.
Nagy, G., et al., "A New Type of Enzyme Electrode: The Ascorbic Acid Eliminator Electrode", *Life Sciences*, vol. 31, No. 23, 1982, pp. 2611-2616.
Nakamura, S., et al., "Effect of Periodate Oxidation on the Structure and Properties of Glucose Oxidase", *Biochimica et Biophysica Acta.*, vol. 445, 1976, pp. 294-308.
Narasimham, K., et al., "p-Benzoquinone Activation of Metal Oxide Electrodes for Attachment of Enzymes", *Enzyme and Microbial Technology*, vol. 7, 1985, pp. 283-286.
Ohara, T. J., "Osmium Bipyridyl Redox Polymers Used in Enzyme Electrodes", *Platinum Metals Review*, vol. 39, No, 2, 1995, pp. 54-62.
Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.
Ohara, T. J., et al., "Glucose Electrodes Based on Cross-Linked $[Os(bpy)_2Cl]^{+/2+}$ Complexed Poly(1-Vinylimidazole) Films", *Analytical Chemistry*, vol. 65, No. 23, 1993, pp. 3512-3517.
Olievier, C. N., et al., "In Vivo Measurement of Carbon Dioxide Tension with a Miniature Electrodes", *Pflugers Archiv: European Journal of Physiology*, vol. 373, 1978, pp. 269-272.
Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.
Palleschi, G., et al., "A Study of Interferences in Glucose Measurements in Blood by Hydrogen Peroxide Based Glucose Probes", *Analytical Biochemistry*, vol. 159, 1986, pp. 114-121.
Pankratov, I., et al., "Sol-Gel Derived Renewable-Surface Biosensors", *Journal of ElectroAnalytical Chemistry*, vol. 393, 1995, pp. 35-41.
Pathak, C., et al., "Rapid Photopolymerization of Immunoprotective Gels in Contact with Cells and Tissue", *Journal of the American Chemical Society*, vol. 114, No. 21, 1992, pp. 8311-8312.
Pickup, J., "Developing Glucose Sensors for In Vivo Use", *Tibtech*, vol. 11, 1993, pp. 285-291.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.

(56) References Cited

OTHER PUBLICATIONS

Pickup, J., et al., "Potentially-Implantable, Amperometric Glucose Sensors with Mediated Electron Transfer: Improving the Operating Stability", *Biosensors*, vol. 4, 1989, pp. 109-119.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.
Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.
Poitout, V., et al., "In Vitro and In Vivo Evaluation in Dogs of a Miniaturized Glucose Sensor", *ASAIO Transactions*, vol. 37, No. 3, 1991, pp. M298-M300.
Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Reach, G., et al., "Can Continuous Glucose Monitoring Be Used for the Treatment of Diabetes?", *Analytical Chemistry*, vol. 64, No. 6, 1992, pp. 381-386.
Rebrin, K., et al., "Automated Feedback Control of Subcutaneous Glucose Concentration in Diabetic Dogs", *Diabetologia*, vol. 32, 1989, pp. 573-576.
Reusch, W., "Other Topics: Organometallic Chemistry: Organometallic Compounds: Main Group Organometallic Compounds," *Virtual Textbook of Organic Chemistry*, 1999, Rev. 2007, 25 pages.
Roe, J. N., et al., "Bloodless Glucose Measurements", *Critical Review in Therapeutic Drug Carrier Systems*, vol. 15, Issue 3, 1998, pp. 199-241.
Sacks (Ed), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Samuels, G. J., et al., "An Electrode-Supported Oxidation Catalyst Based on Ruthenium (IV). pH 'Encapsulation' in a Polymer Film", *Journal of the American Chemical Society*, vol. 103, No. 1981, pp. 307-312.
Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.
Scheller, F. W., et al., "Second Generation Biosensors," *Biosensors & Bioelectronics*, vol. 6, 1991, pp. 245-253.
Scheller, F., et al., "Enzyme Electrodes and Their Application", *Philosophical Transactions of the Royal Society of London B*, vol. 316, 1987, pp. 85-94.
Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.
Schmidt, F. J., et al., "Calibration of a Wearable Glucose Sensor", *The International Journal of Artificial Organs*, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", *Proceeding of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioclectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sittampalam, G., et al., "Surface-Modified Electrochemical Detector for Liquid Chromatography", *Analytical Chemistry*, vol. 55, No. 9, 1983, pp. 1608-1610.
Skoog, D. A., et al., "Evaluation of Analytical Data," *Fundamentals of Analytical Chemistry*, 1966, pp. 55.
Soegijoko, S., et al., "External Artificial Pancreas: A New Control Unit Using Microprocessor", *Hormone and Metabolic Research Supplement Series*, vol. 12, 1982, pp. 165-169.
Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.
Sternberg, F., et al., "Calibration Problems of Subcutaneous Glucosensors when Applied 'In-Situ' in Man", *Hormone and Metabolic Research*, vol. 26, 1994, pp. 523-526.
Sternberg, R., et al., "Covalent Enzyme Coupling on Cellulose Acetate Membranes for Glucose Sensor Development", *Analytical Chemistry*, vol. 60, No. 24, 1988, pp. 2781-2786.
Sternberg, R., et al., "Study and Development of Multilayer Needle-Type Enzyme-Based Glucose Microsensors", *Biosensors*, vol. 4, 1988, pp. 27-40.
Suekane, M., "Immobilization of Glucose Isomerase", *Zettschrift fur Allgemeine Mikrobiologie*, vol. 22, No. 8, 1982, pp. 565-576.
Tajima, S., et al., "Simultaneous Determination of Glucose and 1,5-Anydroglucitol", *Chemical Abstracts*, vol. 111, No. 25, 1989, pp. 394.
Takamura, A., et al., Drug release from Poly(vinyl alcohol) Gel Prepared by Freeze-Thaw Procedure, *Journal of Controlled Release*, vol. 20, 1992, pp. 21-27.
Tarasevich, M. R., "Bioelectrocatalysis", *Comprehensive Treatise of Electrochemistry*, vol. 10, 1985, pp. 231-295.
Tatsuma, T., et al., "Enzyme Monolayer- and Bilayer-Modified Tin Oxide Electrodes for the Determination of Hydrogen Peroxide and Glucose", *Analytical Chemistry*, vol. 61, No. 21, 1989, pp. 2352-2355.
Taylor, C., ct al., "'Wiring' of Glucose Oxidase Within a Hydrogel Made with Polyvinyl Imidazole Complexed with [(Os-4,4'-dimethoxy-2,2'-bipyridine)Cl]$^{+/2+}$", *Journal of ElectroAnalytical Chemistry*, vol. 396, 1995, pp. 511-515.

(56) References Cited

OTHER PUBLICATIONS

Thompson, M., et al., "In Vivo Probes: Problems and Perspectives", *Clinical Biochemistry*, vol. 19, 1986, pp. 255-261.
Trojanowicz, M., et al., "Enzyme Entrapped Polypyrrole Modified Electrode for Flow-Injection Determination of Glucose", *Biosensors & Bioelectronics*, vol. 5, 1990, pp. 149-156.
Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.
Turner, A., et al., "Diabetes Mellitus: Biosensors for Research and Management", *Biosensors*, vol. 1, 1985, pp. 85-115.
Turner, R. F., et al., "A Biocompatible Enzyme Electrode for Continuous in vivo Glucose Monitoring in Whole Blood", *Sensors and Actuators B*, vol. 1, 1990, pp. 561-564.
Tuzhi, P., et al., "Constant Potential Pretreatment of Carbon Fiber Electrodes for In Vivo Electrochemistry", *Analytical Letters*, vol. 24, No. 6, 1991, pp. 935-945.
Umana, M., "Protein-Modified Electrochemically Active Biomaterial Surface", *U.S. Army Research Office, Analytical and Chemical Sciences Research Triangle Institute*, 1988, pp. 1-9.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Urban, G., et al., "Miniaturized Thin-Film Biosensors Using Covalently Immobilized Glucose Oxidase", *Biosensors & Bioelectronics*, vol. 6, 1991, pp. 555-562.
Velho, G., et al., "In Vitro and In Vivo Stability of Electrode Potentials in Needle-Type Glucose Sensors", *Diabetes*, vol. 38, No. 2, 1989, pp. 164-171.
Velho, G., et al., "Strategies for Calibrating a Subcutaneous Glucose Sensor", *Biomedica Biochimica Acta*, vol. 48, 1989, pp. 957-964.
Von Woedtke, T., et al., "In Situ Calibration of Implanted Electrochemical Glucose Sensors", *Biomedica Biochimica Acta*, vol. 48, 1989, pp. 943-952.
Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.
Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.
Wang, D. L., et al., "Miniaturized Flexible Amperometric Lactate Probe", *Analytical Chemistry*, vol. 65, No. 8, 1993, pp. 1069-1073.
Wang, J., et al., "Activation of Glassy Carbon Electrodes by Alternating Current Electrochemical Treatment", *Analytica Chimica Acta*, vol. 167, 1985, pp. 325-334.
Wang, J., et al., "Amperometric Biosensing of Organic Peroxides with Peroxidase-Modified Electrodes", *Analytica Chimica Acta*, vol. 254, 1991, pp. 81-88.
Wang, J., et al., "Screen-Printable Sol-Gel Enzyme-Containing Carbon Inks", *Analytical Chemistry*, vol. 68, No. 15, 1996, pp. 2705-2708.
Wang, J., et al., "Sol-Gel-Derived Metal-Dispersed Carbon Composite Amperometric Biosensors", *Electroanalysis*, vol. 9, No. 1, 1997, pp. 52-55.
Williams, D. L., et al., "Electrochemical-Enzymatic Analysis of Blood Glucose and Lactate", *Analytical Chemistry*, vol. 42, No. 1, 1970, pp. 118-121.
Wilson, G. S., et al., "Progress Toward the Development of an Implantable Sensor for Glucose", *Clinical Chemistry*, vol. 38, No. 9, 1992, pp. 1613-1617.
Yabuki, S., et al., "Electro-Conductive Enzyme Membrane", *Journal of the Chemical Society, Chemical Communications*, 1989, pp. 945-946.
Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.
Yang, L., et al., "Determination of Oxidase Enzyme Substrates Using Cross-Flow Thin-Layer Amperometry", *Electroanalysis*, vol. 8, No. 8-9, 1996, pp. 716-721.
Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.
Yao, T., "A Chemically-Modified Enzyme Membrane Electrode as an Amperometric Glucose Sensor", *Analytical Chimica Acta*, vol. 148, 1983, pp. 27-33.
Ye, L., et al., "High Current Density 'Wired' Quinoprotein Glucose Dehydrogenase Electrode", *Analytical Chemistry*, vol. 65 No. 3, 1993, pp. 238-241.
Yildiz, A., et al., "Evaluation of an Improved Thin-Layer Electrode", *Analytical Chemistry*, vol. 40, No. 7, 1968, pp. 1018-1024.
Zamzow, K., et al., "New Wearable Continuous Blood Glucose Monitor (BGM) and Artificial Pancreas (AP)", *Diabetes*, vol. 39, 1990, pp. 5A-20.
Zhang, Y., et al., "Application of Cell Culture Toxicity Tests to the Development of Implantable Biosensors", *Biosensors & Bioelectronics*, vol. 6, 1991, pp. 653-661.
Zhang, Y., et al., "Elimination of the Acetaminophen Interference in an Implantable Glucose Sensor", *Analytical Chemistry*, vol. 66, No. 7, 1994, pp. 1183-1188.

* cited by examiner

100

METHOD AND SYSTEM FOR PROVIDING CONTEXTUAL BASED MEDICATION DOSAGE DETERMINATION

RELATED APPLICATIONS

The present application claims priority under §35 U.S.C. 119(e) to U.S. provisional patent application No. 60/890,492 filed Feb. 18, 2007, entitled "Method And System For Providing Contextual Based Medication Dosage Determination", and assigned to the Assignee of the present application, Abbott Diabetes Care Inc. of Alameda, Calif., the disclosure of which is incorporated herein by reference for all purposes.

BACKGROUND

With increasing use of pump therapy for Type 1 diabetic patients, young and old alike, the importance of controlling the infusion device such as external infusion pumps is evident. Indeed, presently available external infusion devices typically include an input mechanism such as buttons through which the patient may program and control the infusion device. Such infusion devices also typically include a user interface such as a display which is configured to display information relevant to the patient's infusion progress, status of the various components of the infusion device, as well as other programmable information such as patient specific basal profiles.

The external infusion devices are typically connected to an infusion set which includes a cannula that is placed transcutaneously through the skin of the patient to infuse a select dosage of insulin based on the infusion device's programmed basal rates or any other infusion rates as prescribed by the patient's doctor. Generally, the patient is able to control the pump to administer additional doses of insulin during the course of wearing and operating the infusion device such as for, administering a carbohydrate bolus prior to a meal. Certain infusion devices include a food database that has associated therewith, an amount of carbohydrate, so that the patient may better estimate the level of insulin dosage needed for, for example, calculating a bolus amount.

However, in general, most estimation or calculation of a bolus amount for administration, or a determination of a suitable basal profile, for that matter, are educated estimates based on the patient's physiology as determined by the patient's doctor, or an estimate performed by the patient. Moreover, the infusion devices do not generally include enhancement features that would better assist the diabetic patients to control and/or manage the glucose levels.

In view of the foregoing, it would be desirable to have a method and device for providing insulin therapy determination and recommendation based on real time monitored analyte levels of the patient for proactive insulin therapy treatment to improve management of diabetes. In addition, it would be desirable to have a method and system for providing insulin therapy determination and recommendation based on contextual information including the user or patient's past dosage administration and associated patient physiological conditions.

SUMMARY

In accordance with the various embodiments of the present disclosure, there are provided methods and systems for determining suitable medication dosage levels based on contextual information including prior dosage administration and/or physiological conditions.

DETAILED DESCRIPTION

As described in detail below, in accordance with the various embodiments of the present disclosure, there are provided method and device for determining suitable medication dosage level based on contextual information including user's patient's past dosage administration levels.

Figure 1:
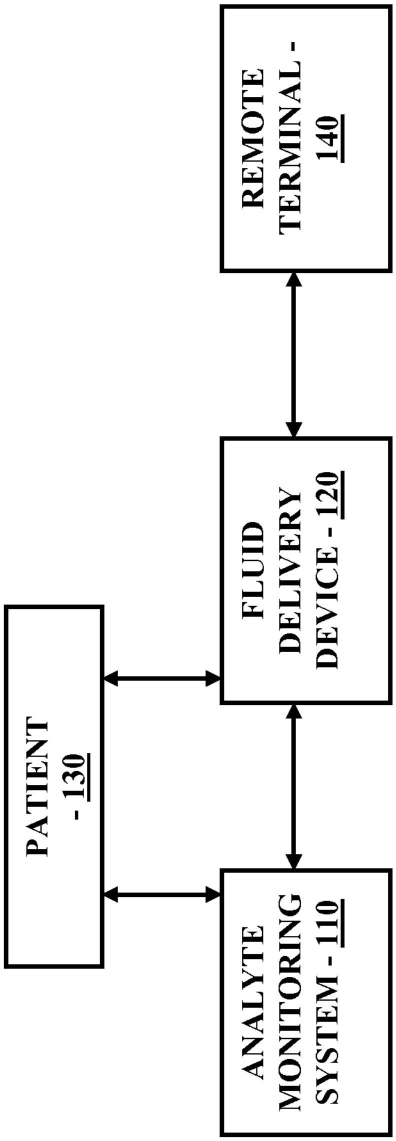
FIG. 1 is a block diagram illustrating a therapy management system for practicing one embodiment of the present disclosure.

FIG. 1 is a block diagram illustrating an insulin therapy management system for practicing one embodiment of the present disclosure. Referring to FIG. 1, the therapy management system 100 includes an analyte monitoring system 110 operatively coupled to a fluid delivery device 120, which may be, in turn, operatively coupled to a remote terminal 140. As shown in the Figure, the analyte monitoring system 110 is, in one embodiment, coupled to the patient 130 so as to monitor or measure the analyte levels of the patient. Moreover, the fluid delivery device 120 is coupled to the patient using, for example, an infusion set and tubing connected to a cannula (not shown) that is placed transcutaneously through the skin of the patient so as to infuse medication such as, for example, insulin, to the patient.

Referring to FIG. 1, in one embodiment the analyte monitoring system 110 may include one or more analyte sensors subcutaneously positioned such that at least a portion of the analyte sensors are maintained in fluid contact with the patient's analytes. The analyte sensors may include, but not limited to, short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 110 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or fluid delivery device 120. That is, over a communication link, the transmitter units may be configured to transmit data associated with the detected analyte levels periodically, and/or intermittently and repeatedly to one or more other devices such as the insulin delivery device and/or the remote terminal 140 for further data processing and analysis.

The transmitter units of the analyte monitoring system 110 may be in one embodiment configured to transmit the analyte related data substantially in real time to the fluid delivery device 120 and/or the remote terminal 140 after receiving it from the corresponding analyte sensors such that the analyte level such as glucose level of the patient 130 may be monitored in real time. In one aspect, the analyte levels of the patient may be obtained using one or more of a discrete blood glucose testing device such as a blood glucose meter, or a continuous analyte monitoring system such as a continuous glucose monitoring system.

Analytes that may be monitored, determined or detected by the analyte monitoring system 110 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Moreover, within the scope of the present disclosure, the transmitter units of the analyte monitoring system 110 may be configured to directly communicate with one or more of the remote terminal 140 or the fluid delivery device 120. Furthermore, within the scope of the present disclosure, additional devices may be provided for communication in the analyte monitoring system 110 including additional receiver/data processing units, remote terminals (such as a physician's terminal and/or a bedside terminal in a hospital environment, for example. In addition, within the scope of the present disclosure, one or more of the analyte monitoring system 110, the fluid delivery device 120 and the remote terminal 140 may be configured to communicate over a wireless data communication link such as, but not limited to, RF communication link, Bluetooth® communication link, infrared communication link, or any other type of suitable wireless communication connection between two or more electronic devices, which may further be uni-directional or bi-directional communication between the two or more devices. Alternatively, the data communication link may include wired cable connection such as, for example, but not limited to, RS232 connection, USB connection, or serial cable connection.

Referring back to FIG. 1, in one embodiment, the analyte monitoring system 100 includes a strip port configured to receive a test strip for capillary blood glucose testing. In one aspect, the glucose level measured using the test strip may in addition, be configured to provide periodic calibration of the analyte sensors of the analyte monitoring system 110 to assure and improve the accuracy of the analyte levels detected by the analyte sensors.

Exemplary analyte systems that may be employed are described in, for example, U.S. Pat. Nos. 6,134,461, 6,175,752, 6,121,611, 6,560,471, 6,746,582, and elsewhere.

Referring again to FIG. 1, the fluid delivery device 120 may include in one embodiment, but not limited to, an external infusion device such as an external insulin infusion pump, an implantable pump, a pen-type insulin injector device, an on-body patch pump, an inhalable infusion device for nasal insulin delivery, or any other type of suitable delivery system. In addition, the remote terminal 140 in one embodiment may include for example, a desktop computer terminal, a data communication enabled kiosk, a laptop computer, a handheld computing device such as a personal digital assistant (PDAs), or a data communication enabled mobile telephone.

Figure 2:
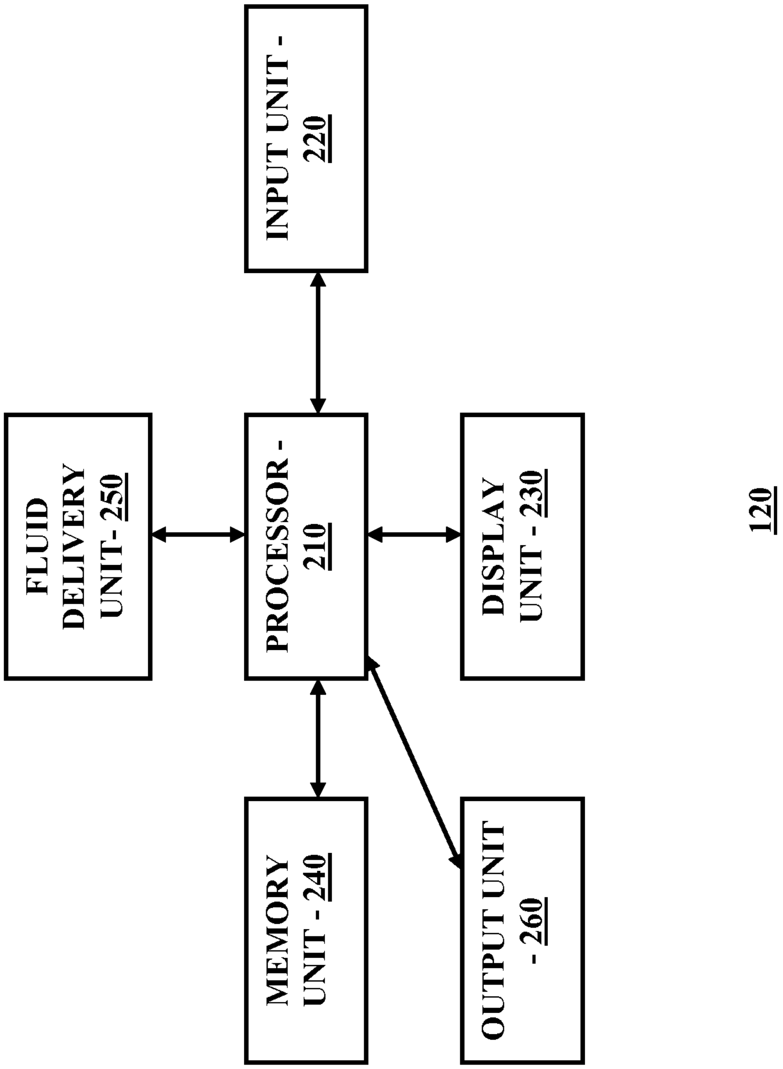
FIG. 2 is a block diagram of a fluid delivery device of FIG. 1 in one embodiment of the present disclosure.

FIG. 2 is a block diagram of an insulin delivery device of FIG. 1 in one embodiment of the present disclosure. Referring to FIG. 2, the fluid delivery device 120 in one embodiment includes a processor 210 operatively coupled to a memory unit 240, an input unit 220, a display unit 230, an output unit 260, and a fluid delivery unit 250. In one embodiment, the processor 210 includes a microprocessor that is configured to and capable of controlling the functions of the fluid delivery device 120 by controlling and/or accessing each of the various components of the fluid delivery device 120. In one embodiment, multiple processors may be provided as a safety measure and to provide redundancy in case of a single processor failure. Moreover, processing capabilities may be shared between multiple processor units within the insulin delivery device 120 such that pump functions and/or control may be performed faster and more accurately.

Referring back to FIG. 2, the input unit 220 operatively coupled to the processor 210 may include a jog dial, key pad buttons, a touch pad screen, or any other suitable input mechanism for providing input commands to the fluid delivery device 120. More specifically, in case of a jog dial input device, or a touch pad screen, for example, the patient or user of the fluid delivery device 120 will manipulate the respective jog dial or touch pad in conjunction with the display unit 230 which performs as both a data input and output units. The display unit 230 may include a touch sensitive screen, an LCD screen, or any other types of suitable display unit for the fluid delivery device 120 that is configured to display alphanumeric data as well as pictorial information such as icons associated with one or more predefined states of the fluid delivery device 120, or graphical representation of data such as trend charts and graphs associated with the insulin infusion rates, trend data of monitored glucose levels over a period of time, or textual notification to the patients.

Referring to FIG. 2, the output unit 260 operatively coupled to the processor 210 may include an audible alarm including one or more tones and/or preprogrammed or programmable tunes or audio clips, or vibratory alert features having one or more pre-programmed or programmable vibratory alert levels. In one embodiment, the vibratory alert may also assist in priming the infusion tubing to minimize the potential for air or other undesirable material in the infusion tubing. Also shown in FIG. 2 is the fluid delivery unit 250 which is operatively coupled to the processor 210 and configured to deliver the insulin doses or amounts to the patient from the insulin reservoir or any other types of suitable containment for insulin to be delivered (not shown) in the fluid delivery device 120 via an infusion set coupled to a subcutaneously positioned cannula under the skin of the patient.

Referring yet again to FIG. 2, the memory unit 240 may include one or more of a random access memory (RAM), read only memory (ROM), or any other types of data storage units that are configured to store data as well as program instructions for access by the processor 210 and execution to control the fluid delivery device 120 and/or to perform data processing based on data received from the analyte monitoring system 110, the remote terminal 140, the patient 130 or any other data input source.

Figure 3:
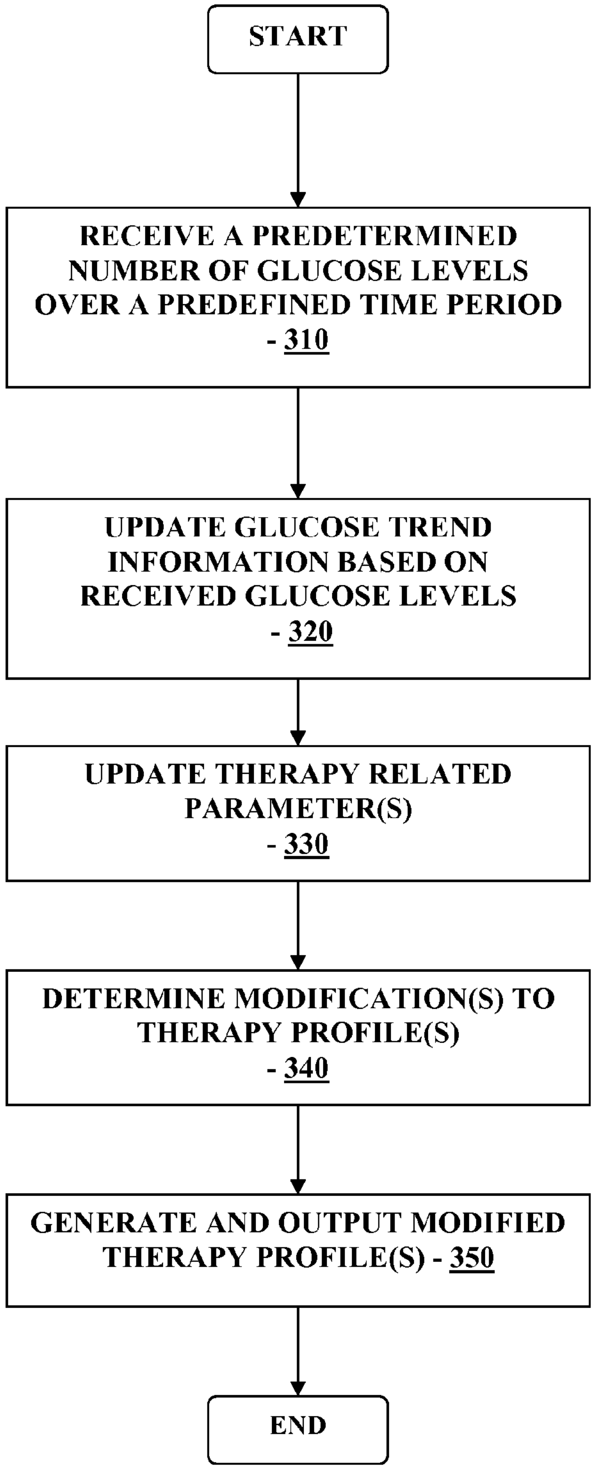
FIG. 3 is a flow chart illustrating therapy management procedure based on real time monitored analyte levels in accordance with one embodiment of the present disclosure.

FIG. 3 is a flow chart illustrating insulin therapy management procedure based on real time monitored analyte levels in accordance with one embodiment of the present disclosure. Referring to FIG. 3, in one embodiment of the present disclosure, a predetermined number of consecutive glucose levels are received or detected over a predetermined or defined time period. For example, in one embodiment, referring to FIG. 1, the monitored glucose level of a patient is substantially continuously received or detected substantially in real time for a predetermined time period. In one embodiment, the predefined time period may include one or more time periods, the data within which may provide a therapeutically meaningful basis for associated data analysis.

That is, the predefined time period of the real time monitored glucose data in one embodiment may include one or more time periods sufficient to provide glucose trend information or sufficient to provide analysis of glucose levels to adjust insulin therapy on an on-going, and substantially real time basis. For example, the predefined time period in one embodiment may include one or more of a 15 minute time period, a 30 minute time period, a 45 minute time period, a one hour time period, a two hour time period and a 6 hour time period. While exemplary predefined time periods are provided herein, within the scope of the present disclosure, any suitable predefined time period may be employed as may be sufficient to be used for glucose trend determination and/or therapy related determinations (such as, for example, modification of existing basal profiles, calculation of temporary basal profile, or determination of a bolus amount).

Referring back to FIG. 3, the consecutive glucose levels received over the predefined time period in one embodiment may not be entirely consecutive due to, for example, data transmission errors and/or one or more of potential failure modes associated with data transmission or processing. As such, in one embodiment of the present disclosure, there is provided a predetermined margin of error for the received real time glucose data such that, a given number of data points associated with glucose levels which are erroneous or alternatively, not received from the glucose sensor, may be ignored or discarded.

Referring back to FIG. 3, upon receiving the predetermined number of glucose levels over a predefined time period, the glucose trend information based on the received glucose levels are updated. For example, in one embodiment, the glucose trend information estimating the rate of change of the glucose levels may be determined, and based upon which the projected level of glucose may be calculated. Indeed, in one embodiment, the glucose trend information may be configured to provide extrapolated glucose level information associated with the glucose level movement based on the real time glucose data received from the glucose sensor. That is, in one embodiment, the real time glucose levels monitored are used to determine the rate at which the glucose levels are either increasing or decreasing (or remaining substantially stable at a given level). Based on such information and over a predetermined time period, a glucose projected information may be determined.

Referring again to FIG. 3, the therapy related parameters associated with the monitored real time glucose levels are updated. That is, in one embodiment, one or more insulin therapy related parameters of an insulin pump such as, but not limited to, insulin on board information associated with the fluid delivery device 120 (FIG. 1), insulin sensitivity level of the patient 130 (FIG. 1), insulin to carbohydrate ratio, and insulin absorption rate. Thereafter, in one embodiment, one or more modifications to the current therapy profile are determined. That is, in one embodiment of the present disclosure, one or more current basal profiles, calculated bolus levels, temporary basal profiles, and/or any other suitable pre-programmed insulin delivery profiles stored in the fluid delivery device 120 (FIG. 1) for example, are retrieved and analyzed based on one or more of the received real time glucose levels, the updated glucose trend information, and the updated therapy related parameters.

Referring back to FIG. 3, after determining one or more modifications to the therapy profiles, the modified one or more therapy profiles are generated and output to the patient 130 (FIG. 1) so that the patient 130 may select, store and/or ignore the one or more modified therapy profiles based on one or more of the monitored real time glucose values, updated glucose trend information, and updated therapy related parameters.

For example, in one embodiment, the patient 130 may be provided with a recommended temporary basal profile based on the monitored real time glucose levels over a predetermined time period as well as the current basal profile which is executed by the fluid delivery device 120 (FIG. 1) to deliver a predetermined level of insulin to the patient 130 (FIG. 1). Alternatively, the patient 130 in a further embodiment may be provided with one or more additional recommended actions for selection as the patient sees suitable to enhance the insulin therapy based on the real time monitored glucose levels. For example, the patient may be provided with a recommended correction bolus level based on the real time monitored glucose levels and the current basal profile in conjunction with, for example, the patient's insulin sensitivity and/or insulin on board information.

In this manner, in one embodiment of the present disclosure, based on real time monitored glucose levels, the patient may be provided with on-going, real time insulin therapy options and modifications to the pre-programmed insulin delivery basal profiles so as to improve upon the initially programmed therapy profiles based on the monitored real time glucose data.

Figure 4:
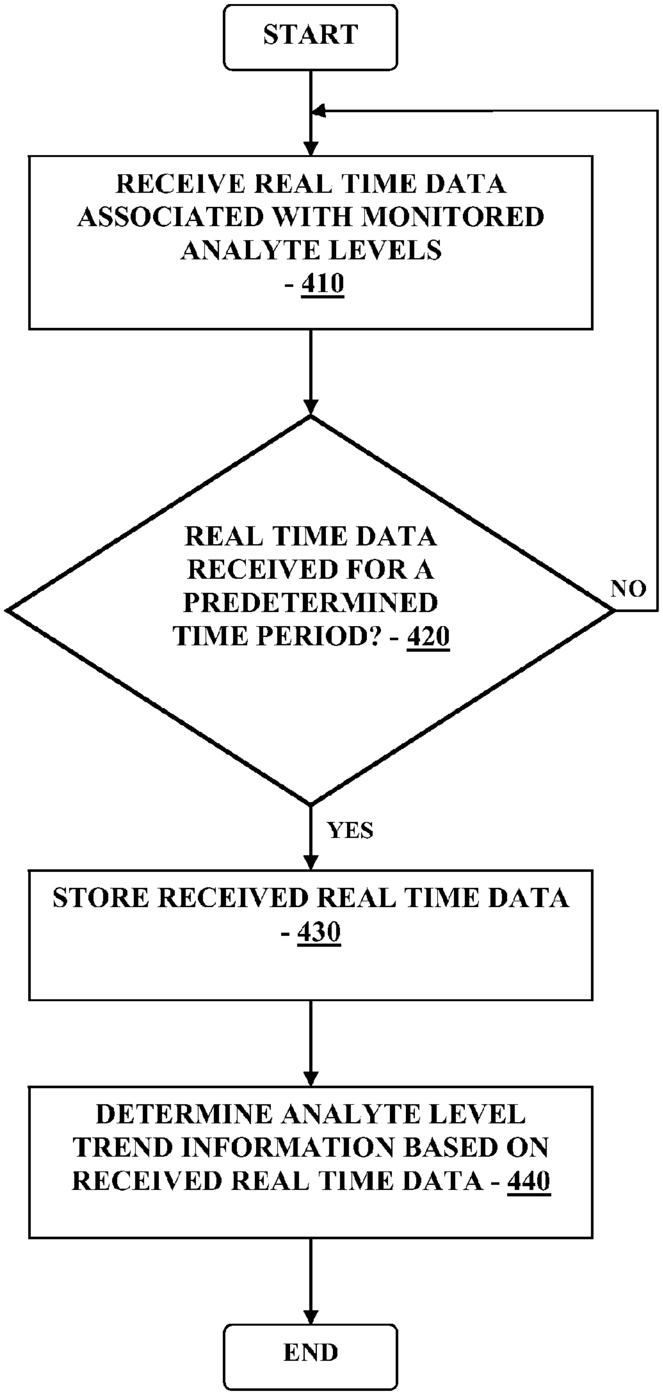
FIG. 4 is a flowchart illustrating analyte trend information updating procedure based on real time monitored analyte levels in accordance with one embodiment of the present disclosure.

FIG. 4 is a flowchart illustrating analyte trend information updating procedure based on real time monitored analyte levels in accordance with one embodiment of the present disclosure. Referring to FIG. 4, in one embodiment, real time data associated with monitored analyte levels is received at step 410. Thereafter it is determined whether the real time data has been received for a predetermined time period at step 420. If it is determined that the real time data has not been received for at least the predetermined time period, then the routine continues to receive the real time data associated with the monitored analyte levels such as glucose levels.

On the other hand, referring back to FIG. 4, if it is determined that the real time data associated with the monitored analyte levels have been received for the predetermined time period (for example, as described above in conjunction with FIG. 3), then, the received real time data associated with the monitored analyte levels are stored at step 430. Thereafter, analyte level trend information is determined based on the received real time data at step 440 associated with the monitored analyte levels.

For example, in one embodiment, the real time data associated with the monitored analyte levels is analyzed and an extrapolation of the data based on the rate of change of the monitored analyte levels is determined. That is, the real time data associated with the monitored analyte levels is used to determined the rate at which the monitored analyte level changed over the predetermined time period, and accordingly, a trend information is determined based on, for example, the determined rate at which the monitored analyte level changed over the predetermined time period.

In a further embodiment, the trend information based on the real time data associated with the monitored analyte levels may be dynamically modified and continuously updated based on the received real time data associated with the monitored analyte levels for one or more predetermined time periods. As such, in one embodiment, the trend information may be configured to dynamically change and be updated continuously based on the received real time data associated with the monitored analyte levels.

Figure 5:
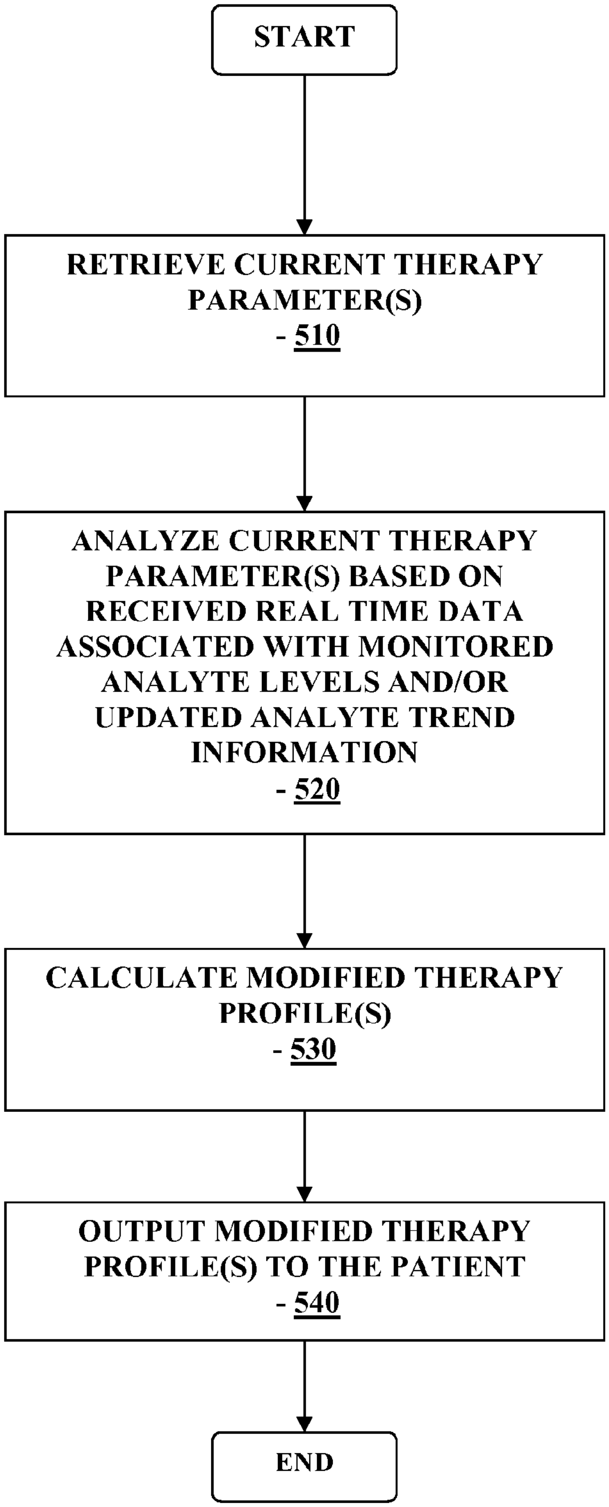
FIG. 5 is a flowchart illustrating modified therapy management procedure based on real time monitored analyte levels in accordance with one embodiment of the present disclosure.

FIG. 5 is a flowchart illustrating modified therapy management procedures based on real time monitored analyte levels in accordance with one embodiment of the present disclosure. Referring to FIG. 5, in one embodiment, the current therapy parameters are retrieved at step 510 and the retrieved current therapy parameters are analyzed based on the received real time data associated with the monitored analyte levels and/or updated analyte trend information at step 520. For example, one or more preprogrammed basal profiles, correction bolus, carbohydrate bolus, temporary basal and associated parameters are retrieved and analyzed based on, for example, the received real time data associated with the monitored analyte levels and/or updated analyte trend information, and further, factoring in the insulin sensitivity of the patient as well as insulin on board information.

Referring to FIG. 5, based upon the analysis of the current therapy parameters, one or more modified therapy profiles are calculated at step 530. That is, based upon the real time glucose levels monitored by the analyte monitoring system 110 (FIG. 1), a modification or adjustment to the pre-programmed basal profiles of the fluid delivery device 120 (FIG. 1) may be determined, and the modified therapy profile is output to the patient 130 (FIG. 1) at step 540. That is, the modification or adjustment to the pre-programmed basal profiles may be provided to the patient for review and/or execution to implement the recommended modification or adjustment to the pre-programmed basal profiles.

In this manner, the patient may be provided with one or more adjustments to the existing or current basal profiles or any other pre-programmed therapy profiles based on continuously monitored physiological levels of the patient such as analyte levels of the patient. Indeed, in one embodiment of the present disclosure, using continuously monitored glucose levels of the patient, modification or adjustment to the pre-programmed basal profiles may be calculated and provided to the patient for review and implementation as desired by the patient. In this manner, for example, a diabetic patient may improve the insulin therapy management and control.

Figure 6:
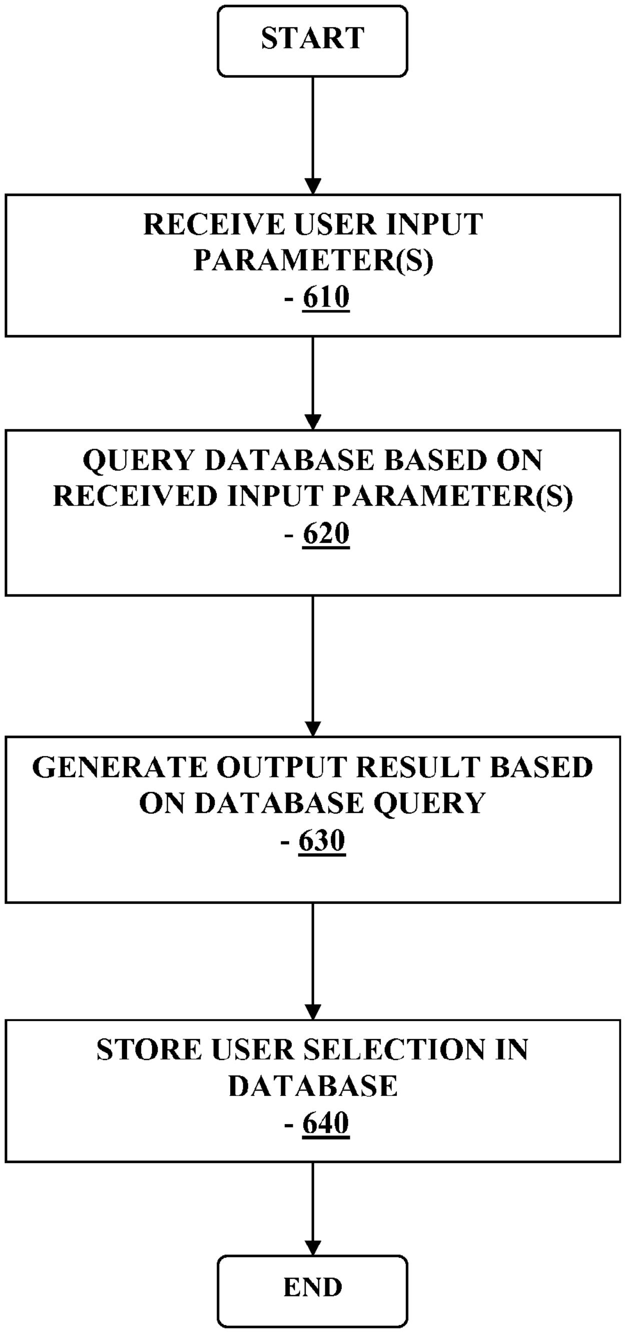
FIG. 6 is a flowchart illustrating contextual based dosage determination in accordance with one embodiment of the present disclosure.

FIG. 6 is a flowchart illustrating contextual based dosage determination in accordance with one embodiment of the present disclosure. Referring to the Figure, one or more user input parameter is received at step 610 such as, for example, the amount of carbohydrate to ingest, type of exercise to perform, current time of day information, or any other appropriate information that may potentially impact the determination of the suitable medication level. Based on the one or more user input parameters, one or more database is queried at step 620. In one embodiment, the database may be provided in the analyte monitoring system 110. Alternatively or in addition, the one or more database may be provided in the fluid delivery device 120 and/or remote terminal 140.

Referring back to FIG. 6, the database query in one embodiment may be configured to search or query for medication dosage levels that are associated with similar parameters as the received one or more user input parameters. Thereafter, the queried result is generated at step 630 and provided to the user which may be acted upon by the user, for example, to administer the medication dosage level based on the queried result. The user selection of the administered medication dosage level is stored in the database at step 640 with the associated one or more user input parameters as well as the time and date information of when the user has administered the medication dosage level.

In this manner, in one embodiment, insulin dosages and associated contextual information (e.g., user input parameters) may be stored and tracked in one or more databases. For example, a bolus amount for a diabetic patient may be determined in the manner described above using historical information without performing a mathematical calculation which takes into account variables, such as sensitivity factors, that vary with time and/or user's physiological conditions, and which may need to be estimated.

In particular, in one embodiment of the present disclosure, insulin dependent users may determine their appropriate insulin dosages by, for example, using historical dosage information as well as associated physiological condition information. For example, the historical data may be stored in one or more databases to allow search or query based on one or more parameters such as the user's physiological condition and other contextual information associated with each prior bolus dosage calculated and administered. In this manner, the user may be advised on the proper amount of insulin under the particular circumstances, the user may be provided with descriptive statistical information of insulin dosages under the various conditions, and the overall system may be configured to learn and customize the dosage determination for the particular user over an extended time period.

For example, in one aspect, contextual information may be stored with the insulin bolus value. The contextual data in one aspect may include one or more of blood glucose concentration, basal rate, type of insulin, exercise information, meal information, carbohydrate content estimate, insulin on board information, and any other parameters that may be used to determine the suitable or appropriate medication dosage level. Some or all of the contextual information may be provided by the user or may be received from another device or devices in the overall therapy management system such as receiving the basal rate information from the fluid delivery device 120 (FIG. 1), or receiving the blood glucose concentration from the analyte monitoring system 110 (FIG. 1).

By way of an example, a contextually determined medication dosage level in one embodiment may be provided to the user along with a suitable or appropriate notification or message to the user that after a predetermined time period since the prior administration of the medication dosage level, the blood glucose level was still above a target level. That is, the queried result providing the suitable medication dosage level based on user input or other input parameters may be accompanied by other relevant physiological condition information associated with the administration of the prior medication dosage administration. In this manner, when the user is provided with the contextually determined medication dosage level, the user is further provided with information associated with the effects of the determined medication dosage level to the user's physiological condition (for example, one hour after the administration of the particular medication dosage level determined, the user's blood glucose level changed by a given amount). Accordingly, the user may be better able to adjust or modify, as desired or needed, the contextually determined medication dosage level to the current physiological conditions.

In this manner, in one embodiment, to determine and provide the user with proper medication dosage levels, the present or current context including the patient's current physiological condition (such as current blood glucose level, current glucose trend information, insulin on board information, the current basal profile, and so on) is considered and the database is queried for one or more medication dosage levels which correlate (for example, within a predetermined range of closeness or similarity) to the one or more current contextual information associated with the user's physiological condition, among others.

Accordingly, in one embodiment, statistical determination of the suitable medication dosage based on contextual information may be determined using, one or more of mean dosage determination, using a standard deviation or other appropriate statistical analysis of the contextual information for medication dosages which the user has administered in the past. Further, in one aspect, in the case where no close match is found in the contextual query for the desired medication dosage level, the medication dosage level with the most similar contextual information may be used to interpolate an estimated medication dosage level.

In still another aspect, the database query may be configured to provide time based weighing of prior medication dosage level determinations such that, for example, more recent dosage level determination in which similar contextual information may be weighed heavier than aged dosage level determination under similar conditions. For example, older or more aged bolus amounts determined may be weighed less heavily than the more recent bolus amounts. Also, over an extended period of time, in one aspect, the older or aged bolus amounts may be aged out or weighed with a value parameter that minimally impacts the current contextual based bolus determination. In this manner, in one aspect, a highly personalized and individualistic profile for medication dosage determination may be developed and stored in the database with the corresponding contextual information associated therewith.

Figure 7:
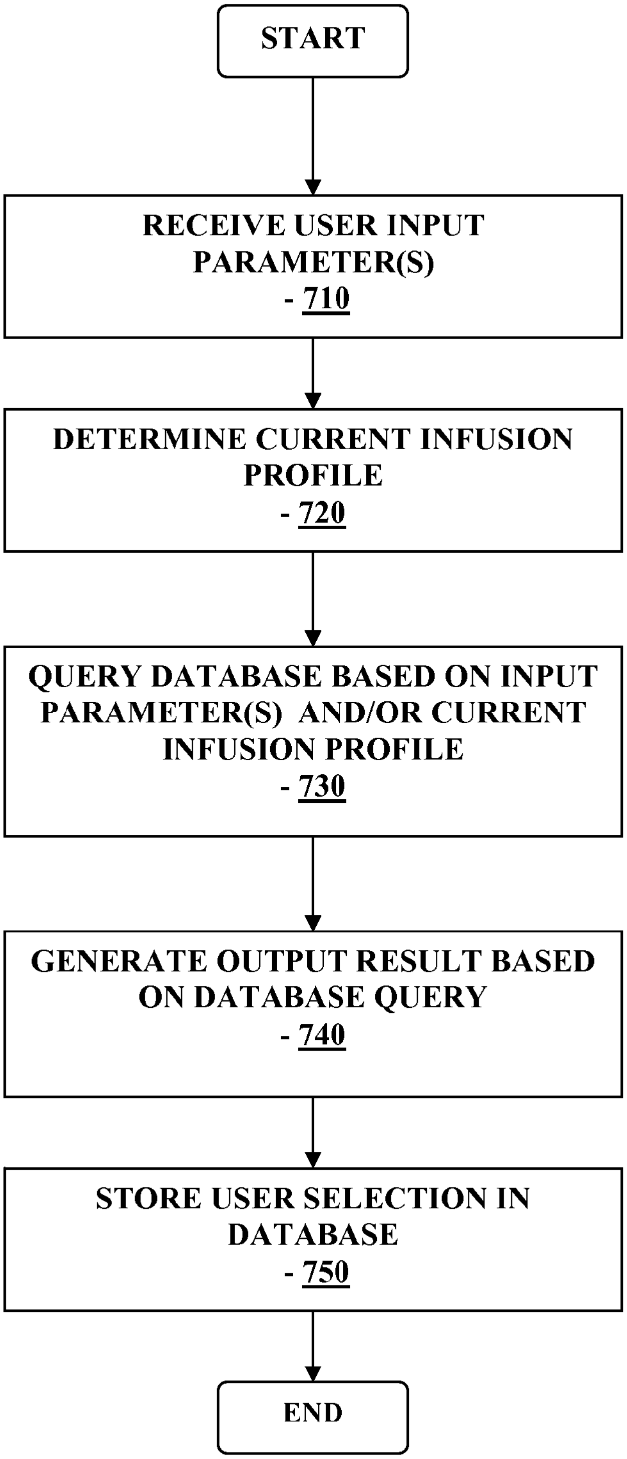
FIG. 7 is a flowchart illustrating contextual based dosage determination in accordance with one embodiment of the present disclosure.

FIG. 7 is a flowchart illustrating contextual based dosage determination in accordance with one embodiment. Referring to FIG. 7, in one aspect, when the user input parameters are received at step 710, the current infusion profile of the user's insulin pump is determined at step 720. Thereafter, the database is queried based on the input parameters and the current infusion profile at step 730, and which results in one or more contextually determined bolus amount associated with the input parameters and the current infusion profile at step 740 that is provided to the user. The determined bolus amount is then stored in the database at step 750 with the associated input parameters and the current infusion profile and any other contextual information associated with the determined bolus amount.

In this manner, in one aspect, in addition to the user provided input parameters, other relevant contextual information may be retrieved (for example, the current infusion profile such as basal rate from the insulin pump, the current blood glucose level and/or glucose trend information from the analyte monitoring system, and the like) prior to the database query to determine the suitable bolus amount.

As discussed above, optionally, the contextual information including the user input parameters and other relevant information may be queried to determine the suitable medication dosage level based on one or more statistical analysis such as, for example, but not limited to, descriptive statistics with the use of numerical descriptors such as mean and standard deviation, or inferential statistics including, for example, estimation or forecasting, correlation of parameters, modeling of relationships between parameters (for example, regression), as well as other modeling approaches such as time series analysis (for example, autoregressive modeling, integrated modeling and moving average modeling), data mining, and probability.

By way of a further non-limiting example, when a diabetic patient plans to ingest insulin of a particular type, the patient enters contextual information such as that the patient has moderately exercised and is planning to consume a meal with a predetermined estimated carbohydrate content. The database in one embodiment may be queried for insulin dosages determined under similar circumstances in the past for the patient, and further, statistical information associated with the determined insulin dosage is provided to the user. In one aspect, the displayed statistical information associated with the determined insulin dosage may include, for example, an average amount of insulin dosage, a standard deviation or a median amount and the $25^{th}$ and the $75^{th}$ percentile values of the determined insulin dosage.

The patient may consider the displayed statistical information associated with the determined insulin dosage, and determine the most suitable or desired insulin amount based on the information received. When the patient programs the insulin pump to administer the desired insulin amount (or otherwise administer the desired insulin amount using other medication administration procedures such as injection (using a pen-type injection device or a syringe), intaking inhalable or ingestable insulin, and the like), the administered dosage level is stored in the database along with the associated contextual information and parameters.

In this manner, the database for use in the contextual based query may be continuously updated with each administration of the insulin dosage such that, each subsequent determination of appropriate insulin dosage level may be determined with more accuracy and is further customized to the physiological profile of the particular patient. Additionally, the database queried may be used for other purposes, such as, for example, but not limited to, tracking medication information, providing electronic history of the patient related medical information, and the like. Further, while the above example is provided in the context of determining an insulin level determination, within the scope of the present disclosure, other medication dosage may be determined based on the contextual based database query approaches described herein.

In a further aspect, the contextual based medication dosage query and determination may be used in conjunction with the standard or available medication dosage determination (for example, standard bolus calculation algorithms) as a supplement to provide additional information or provide a double checking ability to insure that the estimated or calculated bolus or medication dosage level is appropriate for the particular patient under the physiological condition at the time of the dosage level determination.

In still a further aspect, user or patient feedback on current or prior medication dosage levels may be used in conjunction with the contextual based medication dosage query and determination to improve the user or patient's therapy management.

Within the scope of the present disclosure, the processes and routines described in conjunction with FIGS. 3-7 may be performed by the analyte monitoring system 110 (FIG. 1) and/or the fluid delivery device 120 (FIG. 1). Furthermore, the output of information associated with the context based database query for medication dosage determination may be displayed on a display unit of the receiver of the analyte monitoring system 110 (FIG. 1), or the infusion device display of the fluid delivery device 120 (FIG. 1), the display unit of the remote terminal 140 (FIG. 1), or any other suitable output device that is configured to receive the results of the database query associated with the medication dosage level determination. Alternatively, one or more such information may be output to the patient audibly as sound signal output.

In this manner, there are provided methods and system for receiving one or more parameters associated with a user physiological condition, querying a database based on the one or more parameters associated with the user physiological condition, generating a medication dosage amount based on the database query, and outputting the medication dosage amount to the user.

Optionally, statistical analysis may be performed based on the database query and factored into generating the medication dosage amount for the user.

In other aspects, there are provided methods and systems for providing information associated with the direction and rate of change of analyte (e.g., glucose) levels changes for determination of, for example, bolus or basal rate change recommendations, for comparing expected glucose level changes to actual real time glucose level changes to update, for example, insulin sensitivity factor in an ongoing basis, and for automatically confirming the monitored glucose values within a preset time period (e.g., 30 minutes) after insulin therapy initiation to determine whether the initiated therapy is having the intended therapeutic effect.

Indeed, in accordance with the various embodiments of the present disclosure, the use of glucose trend information in insulin delivery rate determinations provides for a more accurate insulin dosing and may lead to a decrease in hypoglycemic events and improved HbA1Cs.

A method in one embodiment includes receiving one or more parameters associated with a physiological condition, querying a database based on the one or more parameters associated with the physiological condition, generating a medication level information based on the database query, and outputting the medication level information.

The database may include a plurality of medication level information and one or more associated parameters for each of the plurality of the medication level information.

The one or more of the plurality of the medication level information stored in the database may include administered medication dosage information, where the administered medication dosage information may include one or more of a past correction bolus amount, a past carbohydrate bolus amount, a past basal profile, or one or more combinations thereof.

Further, querying the database may include performing statistical analysis based on the received one or more parameters, where the statistical analysis may include one or more of mean deviation analysis, standard deviation analysis, estimation analysis, forecasting analysis, correlation of the one or more parameters, modeling of one or more relationships among the one or more parameters, regression analysis, time series analysis, autoregressive modeling, integrated modeling, moving average modeling, data mining, or probability analysis.

The generated medication level information may include one or more of a bolus amount or a basal profile modification for administration to a user.

The method in a further embodiment may include receiving a command associated with the outputted mediation level information.

In another aspect, the method may include executing a therapy related operation based on the outputted medication level information, where the therapy related operation may include generating a command to infuse medication based on the outputted medication level information.

In still another aspect, the method may also include receiving a command confirming administration of a medication amount associated with the outputted medication level information, and storing the outputted medication level information.

The medication level information may be associated with insulin. For example, the medication level information may include a bolus dosage amount, a modification to a predetermined basal profile or a new basal profile for infusing insulin.

The one or more parameters may include one or more of a current glucose level, an insulin sensitivity, a target glucose level, past glucose level, glucose trend information, an amount of carbohydrate to be ingested, insulin on board information, exercise information, time of day information, or one or more combinations thereof.

An apparatus in another embodiment may include one or more processing units, and a memory for storing instructions which, when executed by the one or more processing units, causes the one or more processing units to receive one or more parameters associated with a physiological condition, query the memory based on the one or more parameters associated with the physiological condition, generate a medication level information based on the database query, and output the medication level information.

The memory may include a plurality of medication level information and one or more associated parameters for each of the plurality of the medication level information. In one aspect, the memory may include one or more memory devices including, random access memory (RAM), read-only memory (ROM), electrically erasable programmable read only memory (EEPROM), erasable programmable read-only memory (EPROM), or combinations thereof.

The one or more of the plurality of the medication level information stored in the memory may include administered medication dosage information, where the administered medication dosage information may include one or more of a past correction bolus amount, a past carbohydrate bolus amount, a past basal profile, or one or more combinations thereof.

The memory for storing instructions which, when executed by the one or more processing units, may cause the one or more processing units to perform statistical analysis based on the received one or more parameters, where the statistical analysis may include one or more of mean deviation analysis, standard deviation analysis, estimation analysis, forecasting analysis, correlation of the one or more parameters, modeling of one or more relationships among the one or more parameters, regression analysis, time series analysis, autoregressive modeling, integrated modeling, moving average modeling, data mining, or probability analysis.

The generated medication level information may include one or more of a bolus amount or a basal profile modification for administration to a user.

The memory for storing instructions which, when executed by the one or more processing units, may in another aspect, cause the one or more processing units to receive a command associated with the outputted mediation level information.

The memory for storing instructions which, when executed by the one or more processing units, may cause the one or more processing units to execute a therapy related operation based on the outputted medication level information.

The memory for storing instructions which, when executed by the one or more processing units, may cause the one or more processing units to generate a command to infuse medication based on the outputted medication level information.

The memory for storing instructions which, when executed by the one or more processing units, may cause the one or more processing units to receive a command confirming administration of a medication amount associated with the outputted medication level information, and to store the outputted medication level information.

The medication level information is associated with insulin.

The one or more parameters includes one or more of a current glucose level, an insulin sensitivity, a target glucose level, past glucose level, glucose trend information, an amount of carbohydrate to be ingested, insulin on board information, exercise information, time of day information, or one or more combinations thereof.

In one aspect, the one or more processing units, and the memory are operatively coupled to a medical device, where the medical device may include a blood glucose meter, an analyte monitoring device, or an infusion device. Further, the at least two of the blood glucose meter, the analyte monitoring device or the infusion device may be integrated in a single housing.

A computer program product for enabling one or more processors to perform a database query in a further aspect includes a computer readable medium, and software instructions on the computer readable medium, for enabling the one or more processors to perform predetermined operations comprising receiving one or more parameters associated with a physiological condition, querying a database based on the one or more parameters associated with the physiological condition, generating a medication level information based on the database query, and outputting the medication level information.

Indeed, in one aspect, the medication level information determination and data processings related to the determination may be integrated in the analyte monitoring system 110, the fluid delivery device 120, or the remote terminal 140 (FIG. 1). Alternatively, in networked environment, the memory or database may be located separately from the one or more processing units such that the device incorporating the one or more processing units (such as the fluid delivery device 120 or the analyte monitoring system 110) may be configured to access the information stored in the database or memory in the remote terminal 140 (FIG. 1) over a data network optionally using data encryption, to retrieve and/or store data therein.

A method in another embodiment may include receiving data associated with monitored analyte related levels for a predetermined time period substantially in real time, retrieving one or more therapy profiles associated with the monitored analyte related levels, generating one or more modifications to the retrieved one or more therapy profiles based on the data associated with the monitored analyte related levels.

The method may further include displaying the generated one or more modifications to the retrieved one or more therapy profiles.

In one aspect, the generated one or more modifications to the retrieved one or more therapy profiles may be displayed as one or more of an alphanumeric output display, a graphical output display, an icon display, a video output display, a color display or an illumination display.

In a further aspect, the predetermined time period may include one of a time period between 15 minutes and six hours.

The one or more therapy profiles in yet another aspect may include a basal profile, a correction bolus, a temporary basal profile, an insulin sensitivity, an insulin on board level, and an insulin absorption rate.

In still another aspect, retrieving the one or more therapy profiles associated with the monitored analyte related levels may include retrieving a current analyte rate of change information.

In yet still another aspect, generating the one or more modifications to the retrieved one or more therapy profiles may include determining a modified analyte rate of change information based on the received data associated with monitored analyte related levels.

Moreover, the method may further include generating an output alert based on the modified analyte rate of change information.

Still, the method may also include determining an analyte level projection information based on the modified analyte rate of change information.

A system for providing diabetes management in accordance with another embodiment of the present disclosure includes an interface unit, one or more processors coupled to the interface unit, a memory for storing instructions which, when executed by the one or more processors, causes the one or more processors to receive data associated with monitored analyte related levels for a predetermined time period substantially in real time, retrieve one or more therapy profiles associated with the monitored analyte related levels, and generate one or more modifications to the retrieved one or more therapy profiles based on the data associated with the monitored analyte related levels.

The interface unit may include an input unit and an output unit, the input unit configured to receive the one or more analyte related data, and the output unit configured to output the one or more of the generated modifications to the retrieved one or more therapy profiles.

The interface unit and the one or more processors in a further embodiment may be operatively coupled to one or more of a housing of an infusion device or a housing of an analyte monitoring system.

The infusion device may include one of an external insulin pump, an implantable insulin pump, an on-body patch pump, a pen-type injection device, an inhalable insulin delivery system, and a transdermal insulin delivery system.

The memory in a further aspect may be configured for storing instructions which, when executed by the one or more processors, causes the one or more processors to display the generated one or more modifications to the retrieved one or more therapy profiles.

Further, the memory may be configured for storing instructions which, when executed by the one or more processors, causes the one or more processors to display the generated one or more modifications to the retrieved one or more therapy profiles as one or more of an alphanumeric output display, a graphical output display, an icon display, a video output display, a color display or an illumination display.

In one aspect, the predetermined time period may include one of a time period between 15 minutes and six hours.

The one or more therapy profiles may include a basal profile, a correction bolus, a temporary basal profile, an insulin sensitivity, an insulin on board level, and an insulin absorption rate.

In another aspect, the memory may be further configured for storing instructions which, when executed by the one or more processors, causes the one or more processors to retrieve a current analyte rate of change information.

In still another aspect, the memory may be further configured for storing instructions which, when executed by the one or more processors, causes the one or more processors to determine a modified analyte rate of change information based on the received data associated with monitored analyte related levels.

Additionally, in yet still another aspect, the memory may be further configured for storing instructions which, when executed by the one or more processors, causes the one or more processors to generate an output alert based on the modified analyte rate of change information.

Further, the memory may be further configured for storing instructions which, when executed by the one or more processors, causes the one or more processors to determine an analyte level projection information based on the modified analyte rate of change information.

A system for providing diabetes management in accordance with yet another embodiment of the present disclosure includes an analyte monitoring system configured to monitor analyte related levels of a patient substantially in real time, a medication delivery unit operatively for wirelessly receiving data associated with the monitored analyte level of the patient substantially in real time from the analyte monitoring system, a data processing unit operatively coupled to the one or more of the analyte monitoring system or the medication delivery unit, the data processing unit configured to retrieve one or more therapy profiles associated with the monitored analyte related levels, and generate one or more modifications to the retrieved one or more therapy profiles based on the data associated with the monitored analyte related levels.

In one aspect, the analyte monitoring system may be configured to wirelessly communicate with the medication delivery unit over a radio frequency (RF) communication link, a Bluetooth® communication link, an Infrared communication link, or a local area network (LAN).

The various processes described above including the processes performed by the processor 210 in the software application execution environment in the fluid delivery device 120 as well as any other suitable or similar processing units embodied in the analyte monitoring system 110 and the remote terminal 140, including the processes and routines described in conjunction with FIGS. 3-7, may be embodied as computer programs developed using an object oriented language that allows the modeling of complex systems with modular objects to create abstractions that are representative of real world, physical objects and their interrelationships. The software required to carry out the inventive process, which may be stored in the memory unit 240 (or similar storage devices in the analyte monitoring system 110 and the remote terminal 140) of the processor 210, may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A method, comprising:

receiving one or more parameters associated with a physiological condition;

querying a database for one or more previously determined medication dosage levels administered to a user based on the one or more parameters associated with the physiological condition;

assigning a time based weighted value to each of the one or more previously determined medication dosage levels, wherein the time based weighted value is assigned to each of the one or more previously determined medication dosage levels in a decreasing weighted order based on time such that a more recent medication dosage level is assigned a heavier time based weighted value than an older medication dosage level;

generating a recommended medication dosage level based on the database query, wherein the recommended medication dosage level is based, at least in part, on the one or more previously determined medication dosage levels administered to the user and the time based weighted value assigned to each of the one or more previously determined medication dosage levels;

outputting the recommended medication dosage level including effects of at least one of the one or more previously determined medication dosage levels on the physiological condition on a display device; and updating the database with the recommended medication dosage level when the recommended medication dosage level is administered.

2. The method of claim 1, wherein the database includes a plurality of previously determined medication dosage levels and one or more associated parameters for each of the plurality of the previously determined medication dosage levels.

3. The method of claim 2, wherein one or more of the plurality of the previously determined medication dosage levels stored in the database includes administered medication dosage information.

4. The method of claim 3, wherein the administered medication dosage information includes one or more of a past correction bolus amount, a past carbohydrate bolus amount, a past basal profile, or one or more combinations thereof.

5. The method of claim 1, wherein querying the database includes performing statistical analysis based on the received one or more parameters.

6. The method of claim 5, wherein the statistical analysis includes one or more of mean deviation analysis, standard deviation analysis, estimation analysis, forecasting analysis, correlation of the one or more parameters, modeling of one or more relationships among the one or more parameters, regression analysis, time series analysis, autoregressive modeling, integrated modeling, moving average modeling, data mining, or probability analysis.

7. The method of claim 1, wherein the recommended medication dosage level includes one or more of a bolus amount or a basal profile modification for administration to the user.

8. The method of claim 1, including receiving a user command to administer the recommended mediation dosage level.

9. The method of claim 1, wherein updating the database includes:

receiving confirmation of administration of a medication amount associated with the recommended medication dosage level;

associating the recommended medication dosage level with the one or more parameters; and storing the recommended medication dosage level.

10. The method of claim 1, wherein the one or more previously determined medication dosage levels is associated with insulin.

11. The method of claim 1, wherein the one or more parameters includes one or more of a current glucose level, an insulin sensitivity, a target glucose level, past glucose level, glucose trend information, an amount of carbohydrate to be ingested, insulin on board information, exercise information, time of day information, or one or more combinations thereof.

12. The method of claim 1, further comprising disregarding at least one of the one or more previously determined medication dosage levels when a time frame associated with the at least one of the one or more previously determined medication dosage levels exceeds a time frame threshold.

13. The method of claim 1, further comprising receiving a user modification to the recommended medication dosage level and updating the database when the modified medication dosage level is administered.

14. The method of claim 1, wherein the recommended medication dosage level is a contextually determined medication dosage level.

15. The method of claim 14, wherein the contextually determined medication dosage level includes data corresponding to one or more of a blood glucose concentration level, glucose trend information, a basal profile, a type of insulin, exercise information, meal information, a carbohydrate content estimate, or insulin on board information.

16. The method of claim 1, wherein after a predetermined time period at least one of the one or more previously determined medication dosage levels is assigned a second time based weight value that causes the one or more previously determined medication dosage levels to no longer impact the recommended medication dosage level.

17. An apparatus, comprising:

one or more processing units; and a memory for storing instructions which, when executed by the one or more processing units, causes the one or more processing units to receive one or more parameters associated with a physiological condition, to query the memory for one or more previously determined medication dosage levels administered to a user based on the one or more parameters associated with the physiological condition, to assign a time based weighted value to each of the one or more previously determined medication dosage levels, wherein the time based weighted value is assigned to each of the one or more previously determined medication dosage levels in a decreasing weighted order based on time such that a more recent medication dosage level is assigned a heavier time based weighted value than an older medication dosage level, to generate a recommended medication dosage level based on the query, wherein the recommended medication dosage level is based, at least in part, on the one or more previously determined medication dosage levels administered to the user and the time based weighted value assigned to each of the one or more previously determined medication dosage levels, to output the recommended medication dosage level including effects of at least one of the one or more previously determined medication dosage levels on the physiological condition, and to update the memory with the recommended medication dosage level when the recommended medication dosage level is administered.

18. The apparatus of claim 17, wherein the memory includes a plurality of previously determined medication dosage levels and one or more associated parameters for each of the plurality of the previously determined medication dosage levels.

19. The apparatus of claim 18, wherein one or more of the plurality of the previously determined medication dosage levels stored in the memory includes administered medication dosage information.

20. The apparatus of claim 19, wherein the administered medication dosage information includes one or more of a past correction bolus amount, a past carbohydrate bolus amount, a past basal profile, or one or more combinations thereof.

21. The apparatus of claim 17, wherein the memory for storing instructions which, when executed by the one or more processing units, causes the one or more processing units to perform statistical analysis based on the received one or more parameters.

22. The apparatus of claim 21, wherein the statistical analysis includes one or more of mean deviation analysis, standard deviation analysis, estimation analysis, forecasting analysis, correlation of the one or more parameters, modeling of one or more relationships among the one or more parameters, regression analysis, time series analysis, autoregressive modeling, integrated modeling, moving average modeling, data mining, or probability analysis.

23. The apparatus of claim 17, wherein the recommended medication dosage level includes one or more of a bolus amount or a basal profile modification for administration to the user.

24. The apparatus of claim 17, including receiving a user command to administer the recommended mediation dosage level.

25. The apparatus of claim 17, wherein the memory for storing instructions which, when executed by the one or more processing units, causes the one or more processing units to receive confirmation of administration of a medication amount associated with the recommended medication dosage level, associate the recommended medication dosage level with the one or more parameters, and store the recommended medication dosage level.

26. The apparatus of claim 17, wherein the one or more previously determined medication dosage levels is associated with insulin.

27. The apparatus of claim 17, wherein the one or more parameters includes one or more of a current glucose level, an insulin sensitivity, a target glucose level, past glucose level, glucose trend information, an amount of carbohydrate to be ingested, insulin on board information, exercise information, time of day information, or one or more combinations thereof.

28. The apparatus of claim 17, wherein the one or more processing units, and the memory are operatively coupled to a medical device.

29. The apparatus of claim 28, wherein the medical device includes a blood glucose meter, an analyte monitoring device, an infusion device, or one or more combinations thereof.

30. The apparatus of claim 29, wherein at least two of the blood glucose meter, the analyte monitoring device or the infusion device are integrated in a single housing.

31. The apparatus of claim 17, wherein the memory for storing instructions which, when executed by the one or more processing units, causes the one or more processing units to disregard at least one of the one or more previously determined medication dosage levels when a time frame associated with the at least one of the one or more previously determined medication dosage levels exceeds a time frame threshold.

32. The apparatus of claim 17, wherein the memory for storing instructions which, when executed by the one or more processing units, causes the one or more processing units to receive a user modification to the recommended medication dosage level and update the memory when the modified medication dosage level is administered.

33. The apparatus of claim 17, wherein the recommended medication dosage level is a contextually determined medication dosage level.

34. The apparatus of claim 33, wherein the contextually determined medication dosage level includes data corresponding to one or more of a blood glucose concentration level, glucose trend information, a basal profile, a type of insulin, exercise information, meal information, a carbohydrate content estimate, or insulin on board information.

35. The apparatus of claim 17, wherein after a predetermined time period the memory for storing instructions which, when executed by the one or more processing units, causes the one or more processing units to assign a second time based weight value that causes at least one of the one or more previously determined medication dosage levels to no longer impact the recommended medication dosage level.

36. A computer program product encoded on a non-transitory computer-readable storage medium for enabling one or more processors to perform a database query, the computer program product comprising:

software instructions stored on the computer readable medium for enabling one or more processors to perform predetermined operations comprising:

receiving one or more parameters associated with a physiological condition;

querying a database for one or more previously determined medication dosage levels administered to a user based on the one or more parameters associated with the physiological condition;

assigning a time based weighted value to each of the one or more previously determined medication dosage levels, wherein the time based weighted value is assigned to each of the one or more previously determined medication dosage levels in a decreasing weighted order based on time such that a more recent medication dosage level is assigned a heavier time based weighted value than an older medication dosage level;

generating a recommended medication dosage level based on the database query, wherein the recommended medication dosage level is based, at least in part, on the one or more previously determined medication dosage levels administered to the user and the time based weighted value assigned to each of the one or more previously determined medication dosage levels;

outputting the recommended medication dosage level including effects of at least one of the one or more previously determined medication dosage levels on the physiological condition; and updating the database with the recommended medication dosage level when the recommended medication dosage level is administered.

37. The computer program product of claim 36, further comprising instructions for disregarding at least one of the one or more previously determined medication dosage levels when a time frame associated with the at least one of the one or more previously determined medication dosage levels exceeds a time frame threshold.

38. The computer program product of claim 36, further comprising receiving a user modification to the recommended medication dosage level and updating the database when the modified medication dosage level is administered.

39. The computer program product of claim 36, wherein the recommended medication dosage level is a contextually determined medication dosage level.

40. The computer program product of claim 39, wherein the contextually determined medication dosage level includes data corresponding to one or more of a blood glucose concentration level, glucose trend information, a basal profile, a type of insulin, exercise information, meal information, a carbohydrate content estimate, or insulin on board information.

41. The computer program product of claim 36, wherein after a predetermined time period at least one of the one or more of the previously determined medication dosage levels is assigned a second time based weight value that causes the one or more previously determined medication dosage levels to no longer impact the recommended medication dosage level.

* * * * *